(12) United States Patent
Gatzweiler et al.

(10) Patent No.: US 9,974,306 B2
(45) Date of Patent: May 22, 2018

(54) HERBICIDAL COMBINATIONS FOR TOLERANT SOYBEAN CULTURES

(71) Applicant: BAYER CROPSCIENCE AG, Monheim (DE)

(72) Inventors: Elmar Gatzweiler, Bad Nauheim (DE); Klaus Trabold, Heidelberg (DE); Ralph Dale Bagwell, Duesseldorf (DE); Christian Waldraff, Bad Vilbel (DE); Fabien Poree, Frankfurt (DE)

(73) Assignee: BAYER CROPSCIENCE AG, Manheim (DE)

( * ) Notice: Subject to any disclaimer, the term of this patent is extended or adjusted under 35 U.S.C. 154(b) by 0 days. days.

(21) Appl. No.: 14/438,917

(22) PCT Filed: Nov. 4, 2013

(86) PCT No.: PCT/EP2013/072924
§ 371 (c)(1),
(2) Date: Apr. 28, 2015

(87) PCT Pub. No.: WO2014/072250
PCT Pub. Date: May 15, 2014

(65) Prior Publication Data
US 2015/0272121 A1    Oct. 1, 2015

(30) Foreign Application Priority Data

Nov. 6, 2012 (EP) .................................. 12191443
Nov. 6, 2012 (EP) .................................. 12191450
Nov. 6, 2012 (EP) .................................. 12191459
Nov. 6, 2012 (EP) .................................. 12191464
Nov. 6, 2012 (EP) .................................. 12191473

(51) Int. Cl.
| | |
|---|---|
| *A01N 43/707* | (2006.01) |
| *A01N 43/713* | (2006.01) |
| *A01N 43/82* | (2006.01) |
| *A01N 43/70* | (2006.01) |
| *A01N 41/10* | (2006.01) |
| *A01N 43/56* | (2006.01) |
| *A01N 43/653* | (2006.01) |
| *A01N 43/80* | (2006.01) |

(52) U.S. Cl.
CPC .............. *A01N 43/82* (2013.01); *A01N 41/10* (2013.01); *A01N 43/56* (2013.01); *A01N 43/653* (2013.01); *A01N 43/70* (2013.01); *A01N 43/707* (2013.01); *A01N 43/713* (2013.01); *A01N 43/80* (2013.01)

(58) Field of Classification Search
CPC combination set(s) only.
See application file for complete search history.

(56) References Cited

U.S. PATENT DOCUMENTS

| | | | |
|---|---|---|---|
| 7,612,017 B2 * | 11/2009 | Feucht ................. | A01N 43/707 504/133 |
| 8,592,650 B2 | 11/2013 | Mason et al. | |
| 8,642,748 B2 | 2/2014 | Mason et al. | |
| 2012/0058892 A1* | 3/2012 | Braun .................. | A01N 43/653 504/103 |
| 2012/0304330 A1 | 11/2012 | Mason et al. | |
| 2012/0311743 A1 | 12/2012 | Coulombier et al. | |

FOREIGN PATENT DOCUMENTS

| | | |
|---|---|---|
| WO | 03005820 A1 | 1/2003 |
| WO | 03079789 A1 | 10/2003 |
| WO | 2010000365 A2 | 1/2010 |
| WO | 2011063411 A1 | 5/2011 |
| WO | 2011095460 A1 | 8/2011 |
| WO | 2012007908 A1 | 1/2012 |
| WO | 2012007909 A1 | 1/2012 |
| WO | 2012082548 A2 | 6/2012 |

OTHER PUBLICATIONS

Metribuzin 75DF label, Jan. 20, 2011; retrieved from the Internet on Jul. 29, 2016 :< http://www.cdms.net/Idat/Id6ul000.pdf>.*
Rummens, F.H.A., "An improved definition of synergistic and antagonistic effects," Weed Science, vol. 23(1), pp. 4-6 (1975).*
International Search Report from Corresponding PCT/EP2013/072924, dated Dec. 11, 2013.
Bonny, "Herbicide-tolerant Transgenic Soybean over 15 Years of Cultivation: Pesticide Use, Weed Resistance, and Some Economic Issues. The Case of the USA", Sustainability 2011, 3, 1302-1322; doi:10.3390/su3091302, ISSN 2071-1050, pp. 1302-1322.
Eubank, "Metribuzin-tolerance Screening of Selected Soybean Cultivars" mississippi crops, 2012, 1 page.
Prostko, "Consider metribuzin in soybeans", Crop Productions, www.FarmProgress.com, May 2009, 1 page.

\* cited by examiner

*Primary Examiner* — John Pak
(74) *Attorney, Agent, or Firm* — McBee Moore Woodward & Vanik IP, LLC

(57) ABSTRACT

The invention is in the field of the crop protection products which can be employed against harmful plants in tolerant crops of soybeans and which comprise, as herbicidally active substances, a combination of two or more herbicides.

9 Claims, No Drawings

HERBICIDAL COMBINATIONS FOR TOLERANT SOYBEAN CULTURES

CROSS REFERENCE TO RELATED APPLICATIONS

This application is a § 371 National Stage Application of PCT/EP2013/072924, filed 4 Nov. 2013, which claims priority to EP 12191473.3, filed 6 Nov. 2012, EP 12191443.6, filed 6 Nov. 2012, EP 12191450.1, filed 6 Nov. 2012, EP 12191459.2, filed 6 Nov. 2012 and EP 12191464.2, filed 6 Nov. 2012.

BACKGROUND

Field of the Invention

The invention is in the field of the crop protection products which can be employed against harmful plants in tolerant or resistant crops of soybeans and which comprise, as herbicidally active substances, a combination of two or more herbicides.

Description of Related Art

The introduction of tolerant or resistant soybean varieties and soybean lines, in particular transgenic soybean varieties and soybean lines, adds novel active substances which per se are not selective in conventional soybean varieties, to the conventional weed control system. The active substances are, for example, the known broad-spectrum herbicides such as glyphosate, sulfosate, glufosinate, bialaphos and imidazolinone herbicides, which can nowadays be employed in the tolerant crops developed specifically for them. More recently, soybean lines have been developed, which are tolerant against inhibitors against the hydroxyphenylpyruvate dioxygenase inhibitors ("HPPD inhibitors").

The efficacy of these herbicides against harmful plants in the tolerant crops is high, but depends—similarly to other herbicide treatments—on the nature of the herbicide employed, its application rate, the formulation in question, the nature of harmful plants to be controlled, the climatic conditions, the soil conditions etc. Furthermore, herbicides often exhibit weak points (zero effect) against specific species of harmful plants. Another draw back can be the duration of action, or the degradation rate of the herbicide. If appropriate, changes in the sensitivity of harmful plants, which may occur upon prolonged use of the herbicides or within a geographical limited area, must also be taken into consideration. The loss of activity against individual plants may be compensated for to some extent by higher application rates of the herbicides, if at all. Moreover, there is always a demand for methods to achieve the herbicidal effect with lower application rates of active substances. A lower application rate not only reduces the amount of an active substance required for application, but as a rule, also reduces the amount of formulation auxiliaries required. Both reduce the economic outlay and improve the ecological friendliness of the herbicide treatment.

One possibility for improving the spectrum of activity of a herbicide may consist in combining the active substance with one or more other active substances which contribute the desired additional properties. However, the combined use of a plurality of active substances can lead to phenomena of a chemical, physical and biological incompatibility, for example lacking stability of a coformulation, decomposition of an active substance or antagonism of the active substances. In contrast, what is desired are herbicidal combinations with a favorable profile of action (against a broad spectrum of weed species, incl. the control of weeds which are resistant against various mode of actions or different herbicidal active ingredients out of various chemical groups), possibly high physical and chemical stability, improved speed of activity and a synergistic herbicidal action, which allows the application rate to be reduced and widening of the application window. in comparison with the individual application of the active substances to be combined

SUMMARY

Surprisingly, it has now been found that active substances (A) selected from the group of HPPD inhibitors (HPPDi) in combination with specific soybean herbicides (B), in particular with metribuzin, interact especially favorably when they are employed in such soybean crops which are suitable for the selective use of the first-mentioned herbicides (A). The HPPD inhibitors (A) and the compounds (B) can act synergistically.

DETAILED DESCRIPTION OF A PREFERRED EMBODIMENT

In order to render soybean cultures feasible for treatment with HPPD inhibiting herbicides (A) and/or with the soybean herbicides (B) the soybean cultures must provide a certain level of compatibility with the herbicides (A) and (B). In conjunction with the present invention this compatibility is described as "being tolerant against the herbicides (A) and (B)". A soybean culture which lacks the required compatibility with the herbicides (A) and (B) would be significantly affected, if not completely destroyed, by the application of the herbicides (A) and (B).

In conjunction with the present invention all soybean cultures which comprise a heterologous gene that provides tolerance against HPPD inhibiting active ingredients are deemed "HPPD inhibitor tolerant".

In conjunction with the present invention any kind of HPPDi tolerance gene that renders soybean cultures HPPD inhibitor tolerant can be employed. In an embodiment the HPPDi-tolerant soybean plant contains the hppdPF W336 gene form *Pseudomonas fluorescens* strain A32 which confers tolerance to HPPD-inhibiting herbicides, such as isoxaflutole or the avhppd-03 gene from *Avena* which confers resistance against isoxaflutole or mesotrione. In a preferred embodiment the HPPDi-tolerant soybean plant contains the hppdPF W336 gene form *Pseudomonas fluorescens*.

In a specific aspect of the present invention the terms "tolerant" or "resistant" can be used interchangeably, they describe that the treatment with the herbicide (A) and (B) damages the soybean plants only to a minor extent, or preferably not at all. Minor extent in this regard means that less than 35%, preferably less than 25% most preferably less than 15% of the soybean plants is affected by the herbicide (A) and (B).

It can be observed sometimes that an immediate crop response, for instance yellowing or fading of the leaf surface, does not necessarily affect the final crop yield.

The terms "soybean plant", "soybean crop" and "soybean culture" can be used interchangeably and should encompass all plant parts, such as leafs, sprouts, stems and seeds.

The soybean crops are tolerant or resistant to the herbicide (A), either by genetic modification or due to the joint use of a suitable safener.

The invention also pertains to soybean crops which are tolerant against several herbicides of different modes of action provided that they are tolerant against at least one HPPD inhibitor, Typical examples of such are the SYHT0H2 (tolerant against mesotrione, isoxaflutole, and glufosinate), the EE-GM3 (tolerant against isoxaflutole and glyphosate).

When applying the active substances (A) and (B) on HPPDi tolerant soybean plants either simultaneously or consecutively it has been observed that
(i) the activity against certain weed species is increased synergistically (improved weed control), whereas
(ii) the damage of the soybean crop caused by the herbicides (A) and (B), preferably the damage caused by herbicide (B), is significantly reduced (improved crop selectivity).

The invention therefore relates to use of a herbicidal combinations for controlling harmful plants in soybean crops, wherein the combination contains
(A) an effective amount of at least one, preferably exactly one, active substance with HPPD inhibiting activity selected from the group consisting of
(A1) tembotrione
(A2) mesotrione
(A3) sulcotrione
(A4) isoxafluotole
(A5) topramezone
(A6) bicyclopyrone
(A7) N,O-chelators, according to formula (I)

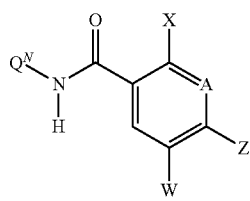

wherein
X is selected from Me, Et, OMe, Cl;
A is C—Y, wherein
Y is selected from SMe, $SO_2Me$, $SO_2Et$, SOMe, SOEt, Pyrazol-1-yl, 4,5-Dihydro-1,2-oxazol-3-yl, $CH_2OMe$, $CH_2OCH_2CF_3$, $CH_2OC_2H_4OMe$, OMe, OEt, OPr, Oi-Bu, $OCH_2$c-Pr, $OC_2H_4OMe$, $O(CH_2)_3OMe$;
Z is selected from $CF_3$, $CHF_2$, $SO_2Me$, $SO_2Et$;
W is hydrogen;
$Q^N$ is

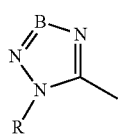

$Q^{N}$-1 wherein
B is nitrogen;
R is selected from Me and Et,
(A8) pyrosulfutole
(A9) tefuryltrione
and
(B) an effective amount of the herbicide metribuzine (B1) and the soybean cultures are tolerant against the active substances (A) and (B) contained in said herbicidal combination.

In one specifically preferred embodiment of the invention metribuzine is replaced by the herbicide atrazine (B2). Hence the invention also relates to the use of a herbicidal combinations for controlling harmful plants in soybean crops, wherein the combination contains
(A) an effective amount of at least one, preferably exactly one, active substance (herbicide) with HPPD inhibiting activity selected from the group consisting of
(A1) tembotrione
(A2) mesotrione
(A3) sulcotrione
(A4) isoxafluotole
(A5) topramezone
(A6) bicyclopyrone or
(A7) N,O-chelators according to formula (I) as defined above
(A8) pyrosulfutole
(A9) tefuryltrione
and
(B) an effective amount of the herbicide atrazine (B2) and the soybean cultures are tolerant against the active ingredients (A) and (B) contained in said herbicidal combination.

In a preferred embodiment of the present invention the N,O-chelator (A7) is selected from the group of substances (A7)1-7, (A7)1-26, (A7)1-60, (A7)1-69 and (A7)1-74 (as defined infra), The herbicidal combination preferably contains a synergistically effective amount of (A) and (B). Optionally the combination can contain one or more, preferably exactly one, further active substances (G).

In a preferred embodiment of the invention, the soybean culture is HPPD inhibitor tolerant, i.e. it contains a heterologous gene that confers tolerance against at least one HPPD inhibitor, In another aspect the invention relates to a method of increasing the yield of soybean cultures comprising applying jointly or separately, pre-planting, pre-emergence, post-emergence or pre- and post-emergence to the plants, parts of the plants, seeds of the plants or the area under cultivation an effective amount of a herbicidal combination comprising or consisting of (A) and (B) and optionally (G).

In a further aspect the invention relates to a method for reducing the abiotic stress of soybean cultures comprising applying jointly or separately, pre-planting, pre-emergence, post-emergence or pre- and post-emergence to the plants, parts of the plants, seeds of the plants or the area under cultivation an effective amount of a herbicidal combination comprising or consisting of (A) and (B) and optionally (G).

In yet another aspect the invention relates to a method for broadening the spectrum of activity of HPPD inhibitors (A) in soybean cultures comprising applying (A) jointly or separately, pre-planting, pre-emergence, post-emergence or pre- and post-emergence to the plants, parts of the plants, seeds of the plants or the area under cultivation with an effective amount of a (B) and optionally (G).

In yet another aspect the invention relates to a method for increasing the tolerance of soybean cultures against HPPD inhibitors (A) comprising applying (A) jointly or separately, pre-planting, pre-emergence, post-emergence or pre- and post-emergence to the plants, parts of the plants, seeds of the plants or the area under cultivation with an effective amount of (B) and optionally (G).

In yet another aspect the invention relates to a method for increasing the selectivity of (B1) metribuzine or (B2) atrazine in soybean cultures comprising applying (B) jointly or separately, pre-planting, pre-emergence, post-emergence or pre- and post-emergence to the plants, parts of the plants, seeds of the plants or the area under cultivation with an effective amount of (A) and optionally (G).

In yet another aspect the invention relates to a method of reducing the damage of HPPD inhibitor tolerant soybean cultures when treated with (B) metribuzine or atrazine comprising applying (B) jointly or separately, pre-planting, pre-emergence, post-emergence or pre- and post-emergence to the plants, parts of the plants, seeds of the plants or the area under cultivation with an effective amount of (A) and optionally (G).

In yet another aspect the invention relates to a method of regulating the growth of soybean plants comprising applying jointly or separately, pre-planting, pre-emergence, post-emergence or pre- and post-emergence to the plants, parts of the plants, seeds of the plants or the area under cultivation an effective amount of a herbicidal combination comprising or consisting of (A) and (B) and optionally (G).

HPPD inhibitors (component (A)) are compounds that inhibit the hydroxyphenylpyruvate dioxygenase (HPPD). HPPD catalyses an early step in the tyrosine degration pathway, that is widely distributed in plants and animals.

In plants inhibition of HPPD affects the formation of homogentisic acid, which is a key precursor for the biosynthesis of both tocopherol (vitamin E) and plastochinone, a critical co-factor in the formation of carotenoids, which protect chlorophyll in plants from being destroyed by sunlight. If this happens, the plants are bleached and the plant dies.

Soybean lines with tolerance against HPPD inhibitors are already known, e.g. from WO2012/082548A2 or WO2011/063411A1. WO2012/082548A2 describes a transgenic soybean plants with the avhppd-03 gene, a mutant HPPD gene derived from *Avena* and a phosphinothricin acetyl transferase gene from *S. viridochromogenes* (the "SYHT0H2 event"). WO2011/063411A1 describes transgenic soybean plants with the "EE-GM3 event", which provide a HPPD inhibitor tolerance and a glyphosate tolerance. In the present invention the herbicical combination is preferably employed in soybean plants with either the SYHT0H2 or the EE-GM3 event or with combinations thereof. The EE-GM 3 event is also known under the designation FG-72.

In another embodiment of the invention the herbicical combination is preferably employed in transgenic soybean plants comprising a chimeric gene encoding a W336 mutant HPPD protein of *Pseudomonas fluorescens* (U.S. Pat. No. 6,245,968) which is preferably fused to the optimized transit peptide for chloroplast targeting (U.S. Pat. No. 5,510,471), and under the control of the 35S CaMV promoter (Odell et al., 1985, Nature 313: 810-812) fused to the 5' enhancer sequence of TEV (Carrington and Freed, 1990, J. Virol. 64: 1590-1597), with as 3' transcript termination and polyadenylation region that of the CaMV 35S gene (Sanfaçon et al., 1991, Genes & Development 5:141-149), abbreviated as "W336 soybean plants" herein. Further examples thereof are described in US2012/0311743A1.

In another embodiment the soybean plant is also tolerant to glyphosate and/or glufosinate and/or to dicamba and/or 2,4-D.

A dicamba tolerant soybean event that could be stacked with the W336 soybean plants is exemplified by MON87708 (US 20110067134 A1).

2,4-D tolerant soybean events that could be stacked with the W336 soybean plants are for instance DAS-44406-6 and DAS-68416-4.

The above mentioned events are only exemplarily listed, generally any other mutant HPPD protein with improved tolerance to HPPDi can also be employed.

The HPPD inhibitors (A1) to (A9) of the herbicidal combinations according to the invention are already known:

(A1) Tembotrione

IUPAC 2-{2-chloro-4-mesyl-3-[(2,2,2-trifluoroethoxy)methyl]benzoyl}cyclohexane-1,3-dione

CAS 335104-84-2

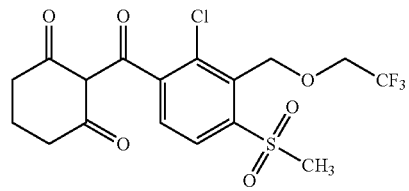 [SMILES: CS(=O)(=O)c1ccc(C(=O)C2C(=O)CCCC2=O)c(Cl)c1COCC(F)(F)F]

Tembotrione belongs to the group of benzoylcyclohexanedione herbicides.

(A2) Mesotrione

IUPAC 2-(4-mesyl-2-nitrobenzoyl)cyclohexane-1,3-dione

CAS 104206-82-8

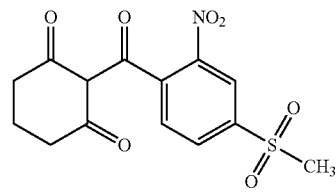 [SMILES: CS(=O)(=O)c1ccc(C(=O)C2C(=O)CCCC2=O)c([N+](=O)[O-])c1]

Mesotrione belongs to the group of benzoylcyclohexanedione herbicides.

(A3) Sulcotrione (the name "chlormesulone" has also been used in the literature, but it has no official status) IUPAC 2-(2-chloro-4-mesylbenzoyl)cyclohexane-1,3-dione

CAS 99105-77-8

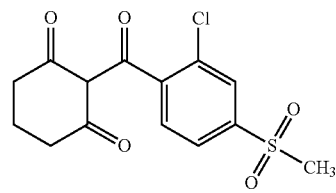 [SMILES: CS(=O)(=O)c1ccc(C(=O)C2C(=O)CCCC2=O)c(Cl)c1]

Sulcotrione belongs to the group of benzoylcyclohexanedione herbicides.

(A4) Isoxafluotole

IUPAC (5-cyclopropyl-1,2-oxazol-4-yl)(α,α,α-trifluoro-2-mesyl-p-tolyl)methanone

CAS 141112-29-0

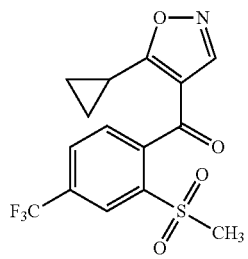 [SMILES: CS(=O)(=O)c1cc(C(F)(F)F)ccc1C(=O)c1cnoc1C1CC1]

Isoxafluotole belongs to the group of cyclopropylisoxazole herbicides.

(A5) Topramezone

IUPAC [3-(4,5-dihydro-1,2-oxazol-3-yl)-4-mesyl-o-tolyl](5-hydroxy-1-methyl pyrazol-4-yl)methanone

CAS 210631-68-8

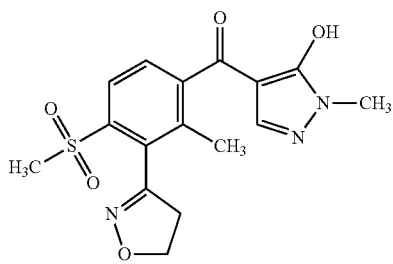

Topramezone belongs to the group of benzoylpyrazole herbicides.

(A6) Bicyclopyrone

IUPAC 4-hydroxy-3-{2-[(2-methoxyethoxy)methyl]-6-(trifluoromethyl)-3-pyridyl carbonyl}bicyclo[3.2.1]oct-3-en-2-one

CAS 352010-68-5

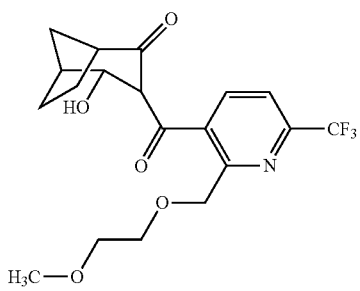 [SMILES: COCCOCc1nc(C(F)(F)F)ccc1C(=O)C1C(=O)C2CCC(C2)C1O]

(A7) N,O chelators

The N,O chelators of the invention and their manufacture are described e.g. in WO2012/028579, WO2011/035874 or WO2012/126932.

The N,O chelators as used according to the invention have the general formula (I)

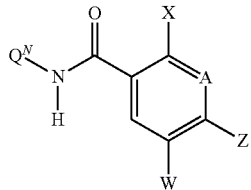

wherein $Q^N$ is:

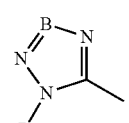    $Q^N$-1

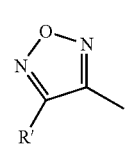    $Q^N$-2

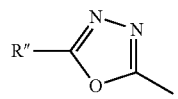    $Q^N$-3 with substituents as defined as follows in tables 1 to 6:

TABLE 1 compounds of the general formula (I), with $Q^N$ as $Q^N$-1, A for CY and B for N and W for hydrogen

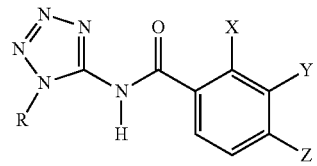

| Nr. | R | X | Y | Z |
|---|---|---|---|---|
| (A7)1-1 | Me | Cl | H | SO$_2$Me |
| (A7)1-2 | Me | SO$_2$Me | H | CF$_3$ |
| (A7)1-3 | Me | Me | SMe | CF$_3$ |
| (A7)1-4 | MeOC$_2$H$_4$ | Me | SMe | CF$_3$ |
| (A7)1-5 | Me | Me | SOMe | CF$_3$ |
| (A7)1-6 | Et | Me | SOMe | CF$_3$ |
| (A7)1-7 | Me | Me | SO$_2$Me | CF$_3$ |
| (A7)1-8 | Et | Me | SO$_2$Me | CF$_3$ |
| (A7)1-9 | Pr | Me | SO$_2$Me | CF$_3$ |
| (A7)1-10 | MeOC$_2$H$_4$ | Me | SO$_2$Me | CF$_3$ |
| (A7)1-11 | Me | Me | SEt | CF$_3$ |
| (A7)1-12 | Et | Me | SEt | CF$_3$ |
| (A7)1-13 | Me | Me | SOEt | CF$_3$ |
| (A7)1-14 | Et | Me | SOEt | CF$_3$ |
| (A7)1-15 | Me | Me | SO$_2$Et | CF$_3$ |
| (A7)1-16 | Et | Me | SO$_2$Et | CF$_3$ |
| (A7)1-17 | Me | Me | SO$_2$Me | Cl |
| (A7)1-18 | Me | Me | SEt | Cl |
| (A7)1-19 | Me | Me | SOEt | Cl |
| (A7)1-20 | Et | Me | SOEt | Cl |
| (A7)1-21 | Me | Me | SO$_2$Et | Cl |
| (A7)1-22 | Me | Me | SMe | Br |
| (A7)1-23 | Me | Me | SEt | Br |
| (A7)1-24 | Me | Me | 4,5-dihydro-1,2-oxazol-3-yl | SO$_2$Me |
| (A7)1-25 | Et | Me | 4,5-dihydro-1,2-oxazol-3-yl | SO$_2$Me |

TABLE 1-continued compounds of the general formula (I), with $Q^N$ as $Q^{N}$-1, A for CY and B for N and W for hydrogen

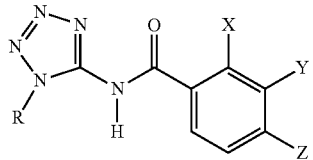

| Nr. | R | X | Y | Z |
|---|---|---|---|---|
| (A7)1-26 | Me | Me | pyrazol-1-yl | SO₂Me |
| (A7)1-27 | Et | Me | pyrazol-1-yl | SO₂Me |
| (A7)1-28 | Me | Me | SMe | SO₂Me |
| (A7)1-29 | Me | Me | SO₂Me | SO₂Me |
| (A7)1-30 | Et | Me | SO₂Me | SO₂Me |
| (A7)1-31 | Me | Me | SO₂Et | SO₂Me |
| (A7)1-32 | Et | Me | SO₂Et | SO₂Me |
| (A7)1-33 | Me | Et | SMe | CF₃ |
| (A7)1-34 | Me | Et | SOMe | CF₃ |
| (A7)1-35 | Me | Et | SO₂Me | CF₃ |
| (A7)1-36 | Me | Et | SMe | Cl |
| (A7)1-37 | Et | Et | SMe | Cl |
| (A7)1-38 | Me | Et | SOMe | Cl |
| (A7)1-39 | Me | Et | SMe | Br |
| (A7)1-40 | Me | Et | SO₂Me | Br |
| (A7)1-41 | Me | Pr | SMe | CF₃ |
| (A7)1-42 | Me | Pr | SOMe | CF₃ |
| (A7)1-43 | Me | c-Pr | SMe | CF₃ |
| (A7)1-44 | Me | OMe | SMe | CF₃ |
| (A7)1-45 | Me | OMe | SOMe | CF₃ |
| (A7)1-46 | Me | OMe | SO₂Me | CF₃ |
| (A7)1-47 | Me | OMe | SEt | CF₃ |
| (A7)1-48 | Me | Cl | SMe | H |
| (A7)1-49 | Me | Cl | SO₂Me | Me |
| (A7)1-50 | Me | Cl | SO₂Et | Me |
| (A7)1-51 | Me | Cl | SO₂Me | CF₃ |
| (A7)1-52 | Me | Cl | OC₂H₄OMe | Cl |
| (A7)1-53 | Me | Cl | SMe | Cl |
| (A7)1-54 | Et | Cl | SMe | Cl |
| (A7)1-55 | Me | Cl | SOMe | Cl |
| (A7)1-56 | Et | Cl | SOMe | Cl |
| (A7)1-57 | Me | Cl | SO₂Me | Cl |
| (A7)1-58 | Et | Cl | SO₂Me | Cl |
| (A7)1-59 | Me | Cl | SO₂Et | Cl |
| (A7)1-60 | Me | Cl | CH₂OMe | SO₂Me |
| (A7)1-61 | Me | Cl | CH₂OCH₂CF₃ | SO₂Me |
| (A7)1-62 | Et | Cl | CH₂OCH₂CF₃ | SO₂Me |
| (A7)1-63 | Me | Cl | CH₂OC₂H₄OMe | SO₂Me |
| (A7)1-64 | Me | Cl | 4,5-dihydro-1,2-oxazol-3-yl | SO₂Me |
| (A7)1-65 | Me | Cl | 4,5-dihydro-1,2-oxazol-3-yl | SO₂Et |
| (A7)1-66 | Me | Cl | 5-methoxymethy-4,5-dihydro-1,2-oxazol-3-yl | SO₂Et |
| (A7)1-67 | Me | Cl | OMe | SO₂Me |
| (A7)1-68 | Me | Cl | OMe | SO₂Et |
| (A7)1-69 | Me | Cl | OEt | SO₂Me |
| (A7)1-70 | Me | Cl | OEt | SO₂Et |
| (A7)1-71 | Me | Cl | OPr | SO₂Me |
| (A7)1-72 | Me | Cl | OPr | SO₂Et |
| (A7)1-73 | Me | Cl | Oi-Bu | SO₂Me |
| (A7)1-74 | Me | Cl | OCH₂c-Pr | SO₂Me |
| (A7)1-75 | Me | Cl | OCH₂c-Pr | SO₂Et |
| (A7)1-76 | Me | Cl | OC₂H₄OMe | SO₂Me |
| (A7)1-77 | Me | Cl | SMe | SO₂Me |
| (A7)1-78 | Me | Me | OMe | SO₂Me |
| (A7)1-79 | Et | OMe | SMe | CHF₂ |
| (A7)1-80 | Me | OMe | SO₂Me | CHF₂ |
| (A7)1-81 | Me | OMe | SMe | CHF₂ |
| (A7)1-82 | Me | OMe | SOMe | CHF₂ |
| (A7)1-83 | Me | Cl | O(CH₂)₃OMe | SO₂Et |
| (A7)1-84 | Et | Cl | SOMe | Me |
| (A7)1-85 | Me | Cl | SMe | CF₃ |

Et = ethyl
Me = Methyl
n-Pr = n-propyl
i-Pr = isopropyl
c-Pr = Cyclopropyl
Ph = Phenyl
Ac = acetyl
i-Bu = isobutyl

TABLE 2 compounds of the general formula (I), with $Q^N$ as $Q^{N}$-1, A for CY and B for CH and W for hydrogen

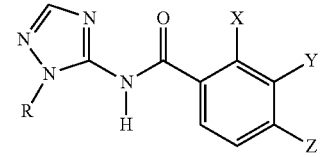

| Nr. | R | X | Y | Z |
|---|---|---|---|---|
| (A7)2-1 | Me | Me | SO₂Me | CF₃ |
| (A7)2-2 | Me | Me | 4,5-dihydro-1,2-oxazol-3-yl | SO₂Me |
| (A7)2-3 | Me | Me | pyrazol-1-yl | SO₂Me |
| (A7)2-4 | Me | Me | SO₂Me | SO₂Me |
| (A7)2-5 | Me | Cl | SO₂Me | Cl |
| (A7)2-6 | Me | Cl | 4,5-dihydro-1,2-oxazol-3-yl | SO₂Me |
| (A7)2-7 | Me | Cl | 4,5-dihydro-1,2-oxazol-3-yl | SO₂Et |
| (A7)2-8 | Me | Cl | OC₂H₄OMe | SO₂Me |
| (A7)2-9 | Me | Cl | SO₂Me | CF₃ |
| (A7)2-10 | Me | Cl | SO₂Et | CF₃ |

Et = Ethyl
Me = methyl
n-Pr = n-propyl
i-Pr = isopropyl
c-Pr = Cyclopropyl
Ph = phenyl
Ac = acetyl
i-Bu = isobutyl

TABLE 3 compounds of the general formula (I), with $Q^N$ as $Q^N$-1, A for CY and B for N

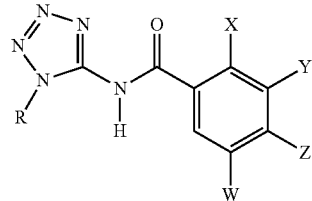

| Nr. | R | X | Y | Z | W |
|---|---|---|---|---|---|
| A3-1 | Me | Cl | H | SMe | Me |
| A3-2 | Me | Cl | SMe | H | Me |
| A3-3 | Me | Cl | SO$_2$Me | H | Me |
| A3-4 | Et | Cl | SO$_2$Me | H | Me |
| A3-5 | Me | Cl | Me | SMe | Me |
| A3-6 | Et | Cl | Me | SO$_2$Me | Me |
| A3-7 | Me | Br | SO$_2$Me | H | Me |

Et = Ethyl
Me = methyl
n-Pr = n-propyl
i-Pr = isopropyl
c-Pr = Cyclopropyl
Ph = phenyl
Ac = acetyl
i-Bu = isobutyl

TABLE 4 compounds of the general formula (I), with $Q^N$ as $Q^N$-1, A for N and B for N and W for hydrogen

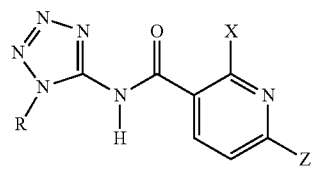

| Nr. | R | X | Z |
|---|---|---|---|
| (A7)4-1 | Me | Me | CF$_3$ |
| (A7)4-2 | Me | CH$_2$OMe | CF$_3$ |
| (A7)4-3 | Et | CH$_2$OMe | CF$_3$ |
| (A7)4-4 | Me | CH$_2$OC$_2$H$_4$OMe | CF$_3$ |
| (A7)4-5 | Et | CH$_2$OC$_2$H$_4$OMe | CF$_3$ |
| (A7)4-6 | Me | CH$_2$OCH$_2$c-Pr | CF$_3$ |
| (A7)4-7 | Me | Cl | CF$_3$ |
| (A7)4-8 | Me | Br | CF$_3$ |
| (A7)4-9 | Me | SO$_2$Me | CF$_3$ |

Et = ethyl
Me = methyl
n-Pr = n-propyl
i-Pr = isopropyl
c-Pr = cyclopropyl
Ph = phenyl
Ac = acetyl
i-Bu = isobutyl

TABLE 5 compounds of the general formula (I), with $Q^N$ as $Q^N$-2, A for CY and W for hydrogen

| Nr. | R' | X | Y | Z |
|---|---|---|---|---|
| (A7)5-1 | Me | Me | SO$_2$Me | SO$_2$Me |
| (A7)5-2 | Me | Me | SO$_2$Me | CF$_3$ |
| (A7)5-3 | Me | Cl | SOMe | CF$_3$ |
| (A7)5-4 | Cl | Cl | SOMe | CF$_3$ |
| (A7)5-5 | Cl | Cl | SO$_2$Me | CF$_3$ |
| (A8)5-6 | Me | Cl | SOMe | SO$_2$Me |
| (A9)5-7 | Me | Cl | SO$_2$Me | CF$_3$ |
| (A10)5-8 | Cl | Cl | pyrazol-1-yl | SO$_2$Me |

Et = ethyl
Me = methyl
n-Pr = n-propyl
i-Pr = isopropyl
c-Pr = cyclopropyl
Ph = phenyl
Ac = acetyl
i-Bu = isobutyl

TABLE 6 compounds of the general formula (I), with $Q^N$ as $Q^N$-2, A for N and W for hydrogen

| Nr. | R" | X | Y | Z |
|---|---|---|---|---|
| (A7)6-1 | Me | Me | SO$_2$Me | CF$_3$ |
| (A7)6-2 | Et | Me | SO$_2$Me | CF$_3$ |
| (A7)6-3 | CH$_2$OMe | Me | SO$_2$Me | CF$_3$ |
| (A7)6-4 | Me | Cl | SO$_2$Me | CF$_3$ |

Et = ethyl
Me = methyl
n-Pr = n-propyl
i-Pr = isopropyl
c-Pr = cyclopropyl
Ph = phenyl
Ac = acetyl
i-Bu = isobutyl Preferred N,O chelators for the invention are (A7)1-7, (A7)1-26, (A7)1-60, (A7)1-69 and (A7)1-74. Particularly preferred are (A7)1-60, (A7)1-69 and (A7)1-74. In a specially preferred embodiment of the invention the N,O chelator is either (A7)1-60 or (A7)1-69.

(A8) Pyrosulfutole
5-hydroxy-1,3-dimethylpyrazol-4-yl)(α,α,α-trifluoro-2-mesyl-p-tolyl)methanone
CAS 365400-11-9

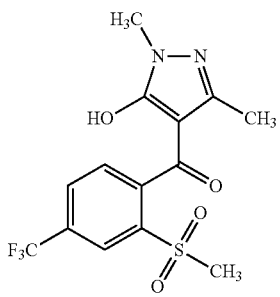 [SMILES: Cc1nn(C)c(O)c1C(=O)c1ccc(C(F)(F)F)cc1S(C)(=O)=O]

(A9) Tefuryltrione
IUPAC 2-{2-chloro-4-mesyl-3-[(RS)-tetrahydro-2-furylmethoxymethyl]benzoyl}cyclohexane-1,3-dione
CAS 473278-76-1

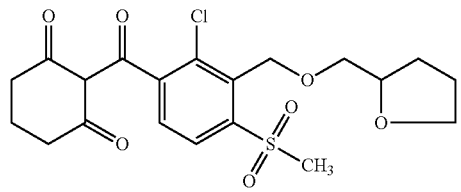 [SMILES: CS(=O)(=O)c1ccc(C(=O)C2C(=O)CCCC2=O)c(Cl)c1COCC1CCCO1]

According to the invention the application rate of the HPPD inhibitors (A1) to (A9) is selected within the ranges subsequently listed with increasing preference:
between 50 and 250 g/ha; 75 and 150 g/ha; 80 and 120 g/ha; 1 and 900 g/ha; 1.5 and 600 g/ha, 5 and 500 g/ha.

Likewise the HPPD inhibitors (herbicide A), also the selective soybean herbicides (herbicide B) as used according to the invention are already known:
(B1) Metribuzin
IUPAC 4-amino-6-tert-butyl-4,5-dihydro-3-methylthio-1,2,4-triazin-5-one or 4-amino-6-tert-butyl-3-methylthio-1,2,4-triazin-5(4H)-one
CAS 21087-64-9

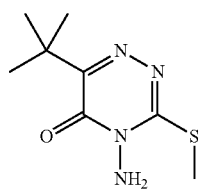

Metribuzine belongs to the group of triazinone herbicides.

According to the invention the application rate of the active ingredient (B1) is selected within the ranges subsequently listed with increasing preference:
50 and 750 g/ha; 150 and 600 g/ha; 200 and 500 g/ha; 10 and 3000 g/ha; 20 and 2000 g/ha; 40 and 1500 g/ha.

(B2) Atrazin
IUPAC 6-chloro-$N^2$-ethyl-$N^4$-isopropyl-1,3,5-triazine-2,4-diamine
CAS 1912-24-9

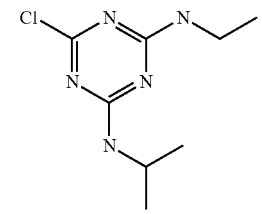

Atrazine belongs to the group of triazinone herbicides.

According to the invention the application rate of the active ingredients (B2)) is selected within the ranges subsequently listed with increasing preference:
50 and 750 g/ha; 150 and 600 g/ha; 200 and 500 g/ha; 200 and 5000 g/ha; 300 and 4000 g/ha; 400 and 3000 g/ha.

The herbicidal combination of the invention comprises at least one component (A) and at least one component (B). In a preferred embodiment the herbicidal combination consists of one component (A) and one component (B) (binary herbicidal combination). The composition (plant protection product) comprising the herbicidal combination of the invention, in particular a binary herbicidal combination, can contain as further components auxiliary substances, adjuvants, or other substances such as colorants and the like which are conventionally used in the formulation of plant protection products.

Preferred binary combinations (C) according to the invention are given in table 7 below. These combinations (C) can optionally contain one or more, in particular one, further active substance (G). Preferred herbicidal combination with (C) and (G), preferably consisting of (C) and (G)—i.e. ternary combinations—are given in table 8 (infra).

TABLE 7

Preferred binary herbicidal combinations; preferred weight ratios of (A) and (B)

| combination Nr. | (A) herbicide | (B) herbicide | preferred weight ratio | more preferred weight ratio | most preferred Weight ratio |
|---|---|---|---|---|---|
| (C1) | (A1) tembotrione | metribuzine | 1:50 to 50:1, preferably 1:3000 to 90:1 | 1:10 to 10:1, preferably 1:1400 to 30:1 | 1:1 to 1:20 preferably 1:300 to 13:1 |

TABLE 7-continued

Preferred binary herbicidal combinations; preferred weight ratios of (A) and (B)

| combination Nr. | (A) herbicide | (B) herbicide | preferred weight ratio | more preferred weight ratio | most preferred Weight ratio |
|---|---|---|---|---|---|
| (C2) | (A2) mesotrione | metribuzine | 1:50 to 50:1; preferably 1:3000 to 90:1 | 1:10 to 10:1; preferably 1:1400 to 30:1 | 1:1 to 1:20, preferably 1:300 to 13:1 |
| (C3) | (A3) sulcotrione | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C4) | (A4) isoxaflutole | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C5) | (A5) topramezone | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C6) | (A6) bicyclopyrone | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C7) | one comp. selected from: (A7)1-1 to (A7)1-85 (A7)2-1 to (A7)2-10 (A7)3-1 to (A7)3-7 (A7)4-1 to (A7)4-9 (A7)5-1 to (A7)5-8 (A7)6-1 to (A7)6-4 | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C8) | (A7)1-7 | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C9) | (A7)1-26 | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C10) | (A7)1-60 | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C11) | (A7)1-69 | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C12) | (A7)1-74 | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C13) | (A8) pyrosulfutole | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C14) | (A9) tefuryltrione | metribuzine | 1:50 to 50:1, preferably 1:3000 to 90:1 | 1:10 to 10:1, preferably 1:1400 to 30:1 | 1:1 to 1:20, preferably 1:300 to 13:1 |
| (C15) | (A1) tembotrione | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C16) | (A2) mesotrione | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C17) | (A3) sulcotrione | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C18) | (A4) isoxaflutole | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C19) | (A5) topramezone | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C20) | (A6) bicyclopyrone | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C21) | one comp. selected from: (A7)1-1 to (A7)1-85 (A7)2-1 to (A7)2-10 (A7)3-1 to (A7)3-7 (A7)4-1 to (A7)4-9 (A7)5-1 to (A7)5-8 (A7)6-1 to (A7)6-4 | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C22) | (A7)1-7 | atrazine | 1:200 to 50:1, preferably 1:5000 to 4:1 | 1:10 to 10:1, preferably 1:2600 to 2:1 | 1:1 to 1:20, preferably 1:600 to 1:1 |

TABLE 7-continued

Preferred binary herbicidal combinations; preferred weight ratios of (A) and (B)

| combination Nr. | (A) herbicide | (B) herbicide | preferred weight ratio | more preferred weight ratio | most preferred Weight ratio |
|---|---|---|---|---|---|
| (C23) | (A7)1-26 | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C24) | (A7)1-60 | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C25) | (A7)1-69 | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C26) | (A7)1-74 | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C27) | (A8) pyrosulfutole | atrazine | 1:200 to 50:1, preferably 1:5000 to 4:1 | 1:10 to 10:1, preferably 1:2600 to 2:1 | 1:1 to 1:20, preferably 1:600 to 1:1 |
| (C28) | (A9) tefuryltrione | atrazine | 1:200 to 50:1, preferably 1:5000 to 4:1 | 1:10 to 10:1, preferably 1:2600 to 2:1 | 1:1 to 1:20, preferably 1:600 to 1:1 |

The favourable effects are observed when the active substances (A) and (B), optionally (G) are applied together, but can also be observed upon split application (splitting). Another possibility is to apply the herbicides or herbicide combinations in several portions (sequential application), for example after pre-emergence applications, followed by post-emergence applications or after early post-emergence applications, followed by applications at medium or late post-emergence. Preferred is the simultaneous application of the active substances of the combination in question, if appropriate in several portions. However, a staggered application of the individual active substances of a combination is also possible and may be advantageous in individual cases. Other crop protection agents such as fungicides, insecticides, acaricides and the like, and/or different auxiliaries, adjuvants and/or fertilizer applications may also be integrated into this system application.

The herbicidal composition can also be employed pre-planting. The use in post-emergence application is most preferred.

Thus, depending on the nature of the herbicides in the herbicidal composition said composition can be applied to the location pre-planting, pre-emergence and/or post emergence. By "pre-planting" it is meant that the herbicide composition is applied before the crop is planted at the location, by "pre-emergence" it is meant that the herbicide composition is applied before the germinating crop plant seed emerges above the location surface and by "post-emergence" it is meant that the herbicide composition is applied once the crop plant is visible above the location surface. These individual use patterns can be applied to the location alone or in any combination. For example, the use pattern could comprise a pre-planting application followed by a post emergence application.

In one embodiment of the invention the favourable effects allow the application rates of the individual active substances to be reduced, a more potent action against the same species of harmful plant combined with the same application rate, the control of species to which the action has hitherto not extended (zero effect), an extended application period and/or a reduced number of required individual applications and—as a result for the user—economical and ecologically more advantageous weed control systems.

For example, the combinations of (A)+(B) (and optionally (G)) according to the invention can allow synergistically increased effects which far and unexpectedly exceed the effects which can be achieved with the individual active substances (A) and (B).

In one preferred embodiment of the invention the combination of herbicides with (A) and (B), in particular the combinations (C) of table 7, can further comprises one or more active substances (G). According to one preferred embodiment the combination consists of (A) and (B)—in particular (C)—and one active substance (G) selected from the list of further active substances (G) below.

In one particularity preferred embodiment of the invention (G) is selected from the group of glufosinate compounds of formula (G1) or the group of glyphosate compounds of formula (G2). (G1) is

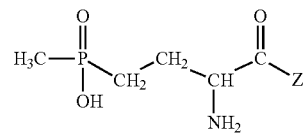

wherein Z is a radical of the formula —OH (glufosinate) or a peptide radical of the formula —NHCH(CH$_3$)CONHCH (CH$_3$)COOH (bialaphos), and their salts and esters.

Formula (G1) encompasses all stereoisomers and their mixtures, in particular the racemate and the particular enantiomer which has a biological action, for example L-glufosinate and its salts. Examples of active substances of the formula (G1) are the following: (G1.1) glufosinate in the narrow sense, i.e. D,L-2-amino-4-[hydroxy(methyl)-phosphinyl]butanoic acid, (G1.2) glufosinate-monoammonium salt, (G1.3) L-glufosinate, L- or (2S)-2-amino-4-[hydroxy (methyl)phosphinyl]butanoic acid (phosphinothricin), (G1.4) L-glufosinate monoammonium salt, (G1.5) bialaphos (or bilanafos), i.e. L-2-amino-4-[hydroxy(methyl)phosphinyl]-butanoyl-L-alanyl-L-alanine, in particular its sodium salt. Glufosinate-monoammonium (G1.2) is the most preferred compound of formula (G1). Glufosinate is usually employed in the form of a salt, preferably of the ammonium salt. The racemate of glufosinate, or glufosinate-ammonium, alone is usually applied at rates between 50 and 2000 g of a.s./ha, usually 100 and 2000 g of a.s./ha (=g of a.i./ ha=grams of active substance per hectare). At such rates, glufosinate is effective mainly when taken up via the green parts of the plants. However, since it is degraded microbially in the soil within a few days, it has no long-term action in the soil. The same also applies to the related active substance bialaphos sodium (also termed bilanafos-sodium); see "The Pesticide Manual" 11th Ed., British Crop Protection Council 1997 pp. 120 121.

As a rule, markedly less active substance (G1), for example an application rate selected within the ranges subsequently listed with increasing preference: 20 to 800, 20 to 600 preferably 40 to 1200, 20 to 1500, 80 to 1000 grams of active substance of glufosinate per hectare (g of a.s./ha or g of a.i./ha) is required in the combinations according to the invention. Similar amounts, preferably amounts which have been converted into moles per hectare, also apply to glufosinate-ammonium and bialafos, or bialafos-sodium.

The combinations with the foliar-acting herbicides (G1) are expediently employed in soybean crops which are resistant or tolerant to the compounds (G1). Some tolerant soybean crops which have been generated by genetic engineering, are already known and are employed in practice; cf. the article in the journal "Zuckerrübe" [Sugarbeet], year 47 (1998), p. 217 et seq.; for the generation of transgenic plants which are resistant to glufosinate, cf. EP-A-0242246, EP-A-242236, EP-A-257542, EP-A-275957, EP-A-0513054). The employment of the herbicidal combinations in soybean plants with the SYHT02 event as described in WO2012/082548 A1 is preferred.

(G2) is

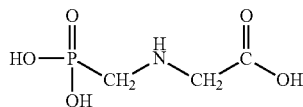

including their salts and esters.

Formula (G2) encompasses glyphosate (G2.1), i.e. N-(phosphonomethyl)glycine, (G2.2) glyphosate-monoisopropylammonium salt, (G2.3) glyphosate-sodium salt, (G2.4) sulfosate, i.e. N-(phosphonomethyl)glycine-trimesium salt=N-(phosphonomethyl)glycine-trimethylsulfoxonium salt. Glyphosate-monoisopropylammonium salt (G2.2) and sulfosate (G2.4) are particularly preferred; most preferred is (G2.2).

Glyphosate is usually employed in the form of a salt, preferably of the monoisopropylammonium salt or the trimethylsulfoxonium salt (=trimesium salt=sulfosate). Based on the free acid glyphosate, the single dose is in the range of 0.020 to 5 kg of a.s./ha, usually 0.05 to 5 kg of a.s./ha.

Glyphosate or the salts thereof are similar to glufosinate with regard to certain applications, but, in contrast to the latter, it is an inhibitor of the enzyme 5-enolpyruvylshikimate-3-phosphate synthase in plants; see "The Pesticide Manual" 11th Ed., British Crop Protection Council 1997 pp. 646 649. In the combinations according to the invention, application rates selected within the ranges subsequently listed with increasing preference: of 20 to 1000, 20 to 800, 20 to 3000, 30 to 2500 most preferable 40 to 1800 g of a.s. glyphosate are, as a rule, required per ha. Also, tolerant plants generated by genetic engineering are known for compounds (G2) and have been introduced into practice; cf. "Zuckerrübe" year 47 (1998), p. 217 et seq.; cf. also WO 92/00377, EP-A-115673, EP-A409815. The employment of the herbicidal combinations in soybean plants with the EE-GM3 event as described in WO2011/063411 A1 is preferred. Preferred combinations comprising (A), (B) and (G), preferably herbicidal combinations consisting of (A), (B) and (G)—i.e. ternary combinations—are given in table 8. Crop protection compositions comprising these ternary combinations can further contain adjuvants, auxiliaries and/ or other additives such as colorants or the like, which are conventionally used for the formulation of plant protection products.

TABLE 8

Preferred ternary combinations (D) with (C) and (G); preferred weight ratios of (A) + (B) and (G)

| | Combination (C) of table 7 | further active substance | preferred weight ratio of (C) and (G) | more preferred weight ratio of (C), and (G) | Most preferred weight ratio of (C), and (G) |
|---|---|---|---|---|---|
| (D1) | (C1) | (G1), preferably (G1.2) | 1:50 to 50:1, preferably 1:100 to 150:1 | 1:50 to 65:1 | 1:1 to 1:20, preferably 1:20 to 25:1 |
| (D2) | (C2) | (G1), preferably (G1.2) | 1:50 to 50:1, preferably 1:100 to 150:1 | 1:10 to 10:1, preferably 1:50 to 65:1 | 1:1 to 1:20 preferably 1:20 to 25:1 |
| (D3) | (C3) | (G1), preferably (G1.2) | 1:50 to 50:1, preferably 1:100 to 150:1 | 1:10 to 10:1, preferably 1:50 to 65:1 | 1:1 to 1:20 preferably 1:20 to 25:1 |
| (D4) | (C4) | (G1), preferably (G1.2) | 1:50 to 50:1, preferably 1:100 to 150:1 | 1:10 to 10:1, preferably 1:50 to 65:1 | 1:1 to 1:20 preferably 1:20 to 25:1 |
| (D5) | (C5) | (G1), preferably (G1.2) | 1:50 to 50:1, preferably 1:100 to 150:1 | 1:10 to 10:1, preferably 1:50 to 65:1 | 1:1 to 1:20 preferably 1:20 to 25:1 |
| (D6) | (C6) | (G1), preferably (G1.2) | 1:50 to 50:1, preferably 1:100 to 150:1 | 1:10 to 10:1, preferably 1:50 to 65:1 | 1:1 to 1:20 preferably 1:20 to 25:1 |
| (D7) | (C7) | (G1), preferably (G1.2) | 1:50 to 50:1, preferably 1:100 to 150:1 | 1:10 to 10:1, preferably 1:50 to 65:1 | 1:1 to 1:20 preferably 1:20 to 25:1 |
| (D8) | (C8) | (G1), preferably (G1.2) | 1:50 to 50:1, preferably 1:100 to 150:1 | 1:10 to 10:1, preferably 1:50 to 65:1 | 1:1 to 1:20 preferably 1:20 to 25:1 |

TABLE 8-continued

Preferred ternary combinations (D) with (C) and (G); preferred weight ratios of (A) + (B) and (G)

| Combination | (C) of table 7 | further active substance | preferred weight ratio of (C) and (G) | more preferred weight ratio of (C), and (G) | Most preferred weight ratio of (C), and (G) |
|---|---|---|---|---|---|
| (D9) | (C9) | (G1), preferably (G1.2) | 1:50 to 50:1, preferably 1:100 to 150:1 | 1:10 to 10:1, preferably 1:50 to 65:1 | 1:1 to 1:20 preferably 1:20 to 25:1 |
| (D10) | (C10) | (G1), preferably (G1.2) | 1:50 to 50:1, preferably 1:100 to 150:1 | 1:10 to 10:1, preferably 1:50 to 65:1 | 1:1 to 1:20 preferably 1:20 to 25:1 |
| (D11) | (C11) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D12) | (C12) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D13) | (C13) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D14) | (C14) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D15) | (C15) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D16) | (C16) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D17) | (C17) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D18) | (C18) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D19) | (C19) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D20) | (C20) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D21) | (C21) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D22) | (C22) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D23) | (C23) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D24) | (C24) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D25) | (C25) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D26) | (C26) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D27) | (C27) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D28) | (C28) | (G1), preferably (G1.2) | 1:50 to 50:1, preferably 1:100 to 150:1 | 1:10 to 10:1, preferably 1:50 to 65:1 | 1:1 to 1:20, preferably 1:20 to 25:1 |
| (D29) | (C1) | (G2), preferably (G2.2) | 1:50 to 50:1, preferably 1:100 to 150:1 | 1:10 to 10:1, preferably 1:100 to 80:1 | 1:1 to 1:20, preferably 1:40 to 50:1 |
| (D30) | (C2) | (G2), preferably (G2.2) | 1:50 to 50:1, preferably 1:100 to 150:1 | 1:10 to 10:1, preferably 1:100 to 80:1 | 1:1 to 1:20, preferably 1:40 to 50:1 |
| (D31) | (C3) | (G2), preferably (G2.2) | 1:50 to 50:1, preferably 1:100 to 150:1 | 1:10 to 10:1, preferably 1:100 to 80:1 | 1:1 to 1:20, preferably 1:40 to 50:1 |
| (D32) | (C4) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |

TABLE 8-continued

Preferred ternary combinations (D) with (C) and (G); preferred weight ratios of (A) + (B) and (G)

| | Combination (C) of table 7 | further active substance | preferred weight ratio of (C) and (G) | more preferred weight ratio of (C), and (G) | Most preferred weight ratio of (C), and (G) |
|---|---|---|---|---|---|
| (D33) | (C5) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D34) | (C6) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D35) | (C7) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D36) | (C8) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D37) | (C9) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D38) | (C10) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D39) | (C11) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D40) | (C12) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D41) | (C13) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D42) | (C14) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D43) | (C15) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D44) | (C16) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D45) | (C17) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D46) | (C18) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D47) | (C19) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D48) | (C20) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D49) | (C21) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D50) | (C22) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D51) | (C23) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D52) | (C24) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D53) | (C25) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D54) | (C26) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D55) | (C27) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |
| (D56) | (C28) | (G2), preferably (G2.2) | 1:50 to 50:1, preferably 1:200 to 150:1 | 1:10 to 10:1, preferably 1:100 to 80:1 | 1:1 to 1:20, preferably 1:40 to 50:1 |

The combinations (D) can be combined with one or more, in particular only one, further active substances (G). These combinations thus contain preferably four active substances (quarternary combinations).

The active substance (G), preferably exactly one active substance, can be selected from the group consisting of the following substances: insecticidally, acaricidally, nematicidally or molluscicidally active ingredients, namely Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, Xylylcarb; Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Triclorfon, Vamidothion, cyclodiene organochlorines, Chlordane, Endosulfan; Ethiprole, Fipronil, Acrinathrin, Allethrin, d-cis-trans Allethrin, d-trans Allethrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(IR) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin, Transfluthrin; DDT; Methoxychlor, Acetamiprid, Clothianidin, Dinotefuran, Imidacloprid, Nitenpyram, Thiacloprid, Thiamethoxam; Nicotine, Spinetoram, Spinosad, Abamectin, Emamectin benzoate, Lepimectin, Milbemectin, Hydroprene, Kinoprene, Methoprene; Fenoxycarb; Pyriproxyfen, Chloropicrin; Sulfuryl fluoride; Borax; Tartar emetic, Pymetrozine; Flonicamid, Clofentezine, Hexythiazox, Diflovidazin, Etoxazole. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, BT crop proteins: Cry1Ab, Cry1Ac, Cry1Fa, Cry2Ab, mCry3A, Cry3Ab, Cry3Bb, Cry34/35Abl, Diafenthiuron, Azocyclotin, Cyhexatin, Fenbutatin oxide; Propargite, Tetradifon, Chlorfenapyr, DNOC, Sulfluramid, Bensultap, Cartap hydrochloride, Thiocyclam, Thiosultap-sodium, Bistrifluron, Chlorfluazuron, Diflubenzuron, Flucycloxuron, Flufenoxuron, Hexaflumuron, Lufenuron, Novaluron, Noviflumuron, Teflubenzuron, Triflumuron, Buprofezin, Cyromazine, Chromafenozide, Halofenozide, Methoxyfenozide, Tebufenozide, Amitraz, Hydramethylnon; Acequinocyl; Fluacrypyrim, Fenazaquin, Fenpyroximate, Pyrimidifen, Pyridaben, Tebufenpyrad, Tolfenpyrad, Rotenone (Derris), Indoxacarb; Metaflumizone, Spirodiclofen, Spiromesifen, Spirotetramat, Aluminium phosphide, Calcium phosphide, Phosphine, Zinc phosphide, Cyenopyrafen, Chlorantraniliprole, Flubendiamide, Amidoflumet, Azadirachtin, Benclothiaz, Benzoximate, Bifenazate, Bromopropylate, Chinomethionat, Cryolite, Cyantraniliprole (Cyazypyr), Cyflumetofen, Dicofol, Diflovidazin, Fluensulfone, Flufenerim, Flufiprole, Fluopyram, Fufenozide, Imidaclothiz, Iprodione, Meperfluthrin, Pyridalyl, Pyrifluquinazon, Tetramethylfluthrin, Iodomethane; products based on *Bacillus firmus* (including but not limited to strain CNCM 1-1582, such as, for example, VOTiVO™, BioNem); 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2(5H)-one (known from WO2007/115644), 4-{[(6-fluoropyridin-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), Flupyradifurone, 4-{[(6-chlor-5-fluoropyridin-3-yl)methyl](methyl)amino}furan-2(5H)-one (known from WO2007/115643), 4-{[(5,6-dichloropyridin-3-yl)methyl](2-fluoroethyl)amino}furan-2(5H)-one (known from WO2007/115646), 4-{[(6-chloro-5-fluoropyridin-3-yl)methyl]-(cyclopropyl)-amino}-furan-2(5H)-one (known from WO2007/115643), 4-{[(6-chloropyridin-3-yl)methyl]-(cyclopropyl)-amino}furan-2(5H)-one (known from EP-A-0 539 588), 4-{[(6-chlorpyridin-3-yl)-methyl](methyl) amino}furan-2(5H)-one (known from EP-A-0 539 588), {[1-(6-chloropyridin-3-yl)ethyl](methyl)oxido-$^4$-sulfanylidene}cyanamide (known from WO2007/149134) and its diastereomers {[(1R)-1-(6-chloropyridin-3-yl)ethyl] (methyl)oxido-$^4$-sulfanylidene}cyanamide (A) and {[(1S)-1-(6-chloropyridin-3-yl)ethyl](methyl)oxido-$^4$-sulfanylidene}cyanamide (B) (also known from WO2007/149134) as well as Sulfoxaflor and its diastereomers [(R)-methyl(oxido){(1R)-1-[6-(trifluoromethyl)pyridin-3-yl] ethyl}-$^4$-sulfanylidene]cyanamide (A1) and [(S)-methyl (oxido) {(1S)-1-[6-(trifluoromethyl)pyridin-3-yl]ethyl}-$^4$-sulfanylidene]cyanamide (A2), referred to as group of diastereomers A (known from WO2010/074747, WO2010/074751), [(R)-methyl(oxido) {(1S)-1-[6-(trifluoromethyl)pyridin-3-yl]ethyl}-$^4$-sulfanylidene]cyanamide (B1) and [(S)-methyl(oxido){(1R)-1-[6-(trifluoromethyl)pyridin-3-yl]ethyl}-$^4$-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluorethyl) sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4, 12b-dimethyl-11-oxo-9-(pyridin-3-yl)-1,3,4,4a,5,6,6a,12, 12a,12b-decahydro-2H,11H-benzo[f]-pyrano[4,3-b] chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N- methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {Γ-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diaza-spiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)-pyridazin-3-yl]-3-azabicyclo[3.2.1]octane (known from WO2007/040280), Flometoquin, PF1364 (CAS-Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-0X0-2-[(2,2,2-trifluoroethyl)amino]-ethyl Jbenzamide (known from WO2005/085216), 4-{[(6-chloropyridin-3-yl)methyl]-(cyclopropyl)amino}-1,3-oxazol-2(5H)-one, 4-{[(6-chloropyridin-3-yl)methyl](2,2-difluoroethyl)-amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazine-carboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl2-[2-({[3-bromo-1-(3-chloropyridin-2-yl)-1H-pyrazol-5-yl]carbonyl}-amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)-benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazine-carboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), N-[2-(5-amino-1,3,4-thiadiazol-2-yl)-4-chloro-6-methylphenyl]-3-bromo-1-(3-chloro-pyridin-2-yl)-1H-pyrazole-5-carboxamide (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

The active substance (G), preferably exactly one active substance (G), can also be selected from the group consisting of the following fungicides, namely aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]-phenyl}-N-ethyl-N-methylimidoformamide, N-ethyl-N-methyl-N'-{2-methyl-5-(trifluoro-methyl)-4-[3-(trimethylsilyl)propoxy]phenyl}imidoformamide, O-[1-(4-methoxyphenoxy)-3,3-dimethylbutan-2-yl]1H-imidazole-1-carbothioate, bixafen, boscalid, carboxin, diflumetorim, fenfuram, fluopyram, flutolanil, fluxapyroxad, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxyl)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxy-imino)-N-methylethanamide, (2E)-2-(methoxy-imino)-N-methyl-2-(2-{[({(1E)-1-[3-(trifluoro-methyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fhioro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2- ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide, (2R)-2-{2-[(2,5-dimethylphenoxy)methyl]phenyl}-2-methoxy-N-methylacetamide, benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine, 3-chloro-5-(6-chloropyridin-3-yl)-6-methyl-4-(2,4,6-trifluorophenyl)pyridazine, bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur, sulphur preparations including calcium polysulphide, thiram, tolylfluanid, zineb, ziram, acibenzolar-S-methyl, isotianil, probenazole, tiadinil, andoprim, blasticidin-S, cyprodinil, kasugamycin, kasugamycin hydrochloride hydrate, mepanipyrim, pyrimethanil, 3-(5-fluoro-3,3,4,4-tetramethyl-3,4-dihydroisoquinolin-1-yl)quinoline, fentin acetate, fentin chloride, fentin hydroxide, silthiofam, benthiavalicarb, dimethomorph, flumorph, iprovalicarb, mandipropamid, polyoxins, polyoxorim, validamycin A, valifenalate, biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene tolclofos-methyl, carpropamid, diclocymet, fenoxanil, phthalide, pyroquilon, tricyclazole, 2,2,2-trifluoroethyl {3-methyl-1-[(4-methylbenzoyl)amino]butan-2-yl}carbamate, benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl, oxolinic acid, chlozolinate, fenpiclonil, fludioxonil, iprodione, procymidone, quinoxyfen, vinclozolil, binapacryl, dinocap, ferimzone, fluazinam, meptyldinocap, benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrine, tebufloquin, tecloftalam, tolnifanide, triazoxide, trichlamide, zarilamid, (3S,6S,7R,8R)-8-benzyl-3-[({3-[(isobutyryloxy)methoxy]-4-methoxypyridin-3-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl Jpiperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-m 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1,2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenyl-acetamide, N—{(Z)-[(cyclopropylmethoxy)imino][6-(difluoromethoxy)-2,3-difluorophenyl]-methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]-amino}oxy)methyl]pyridin-2-yl}carbamate, phenazine-1-carboxylic acid, quinolin-8-ol, quinolin-8-ol sulfate (2:1), tert-butyl {6-[({[(1-methyl-1H-tetrazol-5-yl)(phenyl)methylene]-amino}oxy)methyl]pyridin-2-yl}carbamate, 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'43-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'43-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulfonyl)valinamide, 4-oxo-4-[(2-phenylethyl)amino]butanoic acid, but-3-yn-1-yl {6-[({[(Z)-(1-methyl-1H-tetrazol-5-yl)(phenyl)methylene]amino}oxy)methyl]pyridin-2-yl}carbamate.

The active substance (G), preferably exactly one active substance (G), can also be selected from the group consisting of the following herbicides:
acetochlor, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clethodim, clodinafop, clodinafop-propargyl, clomazone, clomeprop, clopyralid, cloransulam, cloransulam-methyl, cumyluron, cyanamide, cyanazine, cycloate, cyclosulfamuron, cycloxydim, cyhalofop, cyhalofop-butyl, cyprazine, 2,4-D, 2,4-D-butotyl, -butyl, -dimethylammonium, -diolamin, -ethyl, 2-ethylhexyl, dazomet, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, n-decanol, desmedipham, detosyl-pyrazolate (DTP), dicamba, dichlobenil, dichlorprop, dichlorprop-P, diclofop, diclof op-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-5231, i.e. N-{2-chloro-4-fluoro-5-[4-(3-fluoropropyl)-5-oxo-4,5-dihydro-1H-tetrazol-1-yl]phenyl}ethanesulfonamide, F-7967, i. e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet (thiafluamide), flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fluthiamide, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl-(2,4-dichlorophenoxyl)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and sodium, ipfencarbazone, isoproturon, isouron, isoxaben, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, kenacil, kinuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium, and -butotyl, mecoprop-P, mecoprop-P-butotyl, dimethylammonium, -2-ethylhexyl and -potassium, mefenacet, mefluidide, mesosulfuron, mesosulfuron-methyl, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-128, i.e. 6-chloro-N-[(2E)-3-chloroprop-2-en-1-yl]-5-methyl-N-phenylpyridazin-3-amine, MT-5950, i.e. N-(3-chloro-4-isopropylphenyl)-2-methylpentan amide, NGGC-011, napropamide, NC-310, i.e. [5-(benzyloxy)-1-methyl-1H- pyrazol-4-yl](2,4-dichlorophenyl)methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, prifluraline, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, sulfentrazone, sulfometuron, sulfometuron-methyl, sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trichloroacetic acid), TCA-sodium, tebuthiuron, tefuryltrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, tralkoxydim, triafamone, tri-allate, triasulfuron, triaziflam, tribenuron, tribenuron-methyl, triclopyr, trietazine, trifloxysulfuron, trifloxysulfuron-sodium, trifluralin, triflusulfuron, triflusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline; or plant growth regulators selected from the group consisting of zcibenzolar, acibenzolar-S-methyl, 5-aminolevulinic acid, ancymidol, 6-benzylaminopurine, Brassinolid, catechine, chlormequat chloride, cloprop, cyclanilide, 3-(cycloprop-1-enyl) propi-onic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methylcyclopropene, methyl jasmonate, 2-(1-naphthyl)acetamide, 1-naphthylacetic acid, 2-naphthyloxyacetic acid, nitrophenolate-mixture, paclobutrazol, N-(2-phenylethyl)-beta-alanine, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P; or agrochemically preferable salts or other forms thereof.

The following selective soybean herbicides are preferably used as active substances (G) in postemergence applications: Bentazon, acetochlor, aciflurfen, chlorimuron, lactofen, sulfentrazone, thifensulfuron, imazetapyr, imazamox, imazaquin, fomesafen, lactofen, flumetsulam, norflurazon, sethoxidim, clethodim, haloxifop, haloxifop-p-methyl, fluazifop, fluazifop-P, quizalafop, quizalafop-P The following selective soybean herbicides are preferably used as active substances (G) in Preemergence and/or pre-plant applications:
Pendimethalin, clomazone, chloransulam, metolachlor, (S)-metolachlor flumioxazin, chloransulam, flumetsulam, dimethenamid, dimethenamid-p, 2,4 DB, 2,4 D, dicamba, carfentrazone, saflufenacil, linuron, tribenuron, thifensulfuron, Flumioxazin.

The combinations according to the invention have an outstanding herbicidal activity against a broad spectrum of economically important monocotyledonous and dicotyledonous harmful plants including weed species which are resistant against single herbicidal actives and can be controlled only with inventive combinations. The active substances also act efficiently on perennial weeds which produce shoots from rhizomes, rootstocks or other perennial organs and which are difficult to control. In this context, it does not matter whether the substances are applied before sowing, pre-emergence or post-emergence. Post-emergence application, or early post-sowing pre-emergence application, is preferred. Most preferred are post-emergence applications.

These harmful plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avenafatua*), common cocklebur (*Xanthium pensylvanicum*), common lambsquarters (*Chenopodium album*), morning glories (*Ipomoea* spp. like *I. hederacea, I. grandifolia*), pigweed (*Amaranthus* spp.), velvetleaf (*Abutilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spica-venti*), wooly cupgrass (*Erichloa villosa*), yellow nutsedge (*Cyperus esculentus*), common chickweed (*Stellaria media*), common ragweed, giant ragweed (*Ambrosia trifida, Ambrosia artemisiifolia*), kochia(*Kochia scoparia*), horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp sesbania (*Sesbania exaltata*), sicklepod (*Senna obtusifolia*), Texas blueweed (*Helianthus ciliaris*), Fall panicum (*Panicum dichotomiflorum*), Texas panicum (*Panicum texanum*), Broadleaf signalgrass (*Brachiaria*), and Devil's claws (*Proboscidea louisianica*). In other aspects of the invention, the weed comprises an herbicide-resistant ryegrass, for example, a glyphosate resistant ryegrass, a paraquat resistant ryegrass, ACCase-inhibitor resistant ryegrass, and a non-selective herbicide resistant ryegrass.

In another aspect of the invention, methods of controlling volunteer SYHT0H2 or EE-GM3 crop plants at a location are provided wherein the method comprises applying to the location one or more herbicides effective on soybeans and having a mode of action other than inhibition of HPPD.

In another aspect of the invention methods of controlling volunteer transgenic events at a location comprising SYHT0H2 or EE-GM3 crop plants are provided wherein the volunteer events comprise resistance to one or more herbicides but do not comprise resistance to HPPD inhibitors wherein the method comprises applying to the location a controlling amount of an herbicidal composition comprising one or more HPPD inhibitors.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

In comparison with the individual preparations, the herbicidal compositions according to the invention are distinguished by a more rapidly commencing and longer lasting herbicidal action. As a rule, the rainfastness of the active substances in the combinations according to the invention is advantageous. A particular advantage is that the dosages of the compounds (A) and (B), which are used in the combinations and are effective, can be adjusted to such a low quantity that their soil action is optimal. This does not only allow them to be employed in sensitive crops in the first place, but groundwater contaminations are virtually avoided. The active-substance-combination according to the invention allows the application rate of the active substances required to be reduced considerably.

When herbicides of the type (A)+(B) are used jointly, superadditive (=synergistic) effects can be observed. This means that the effect in the combinations exceeds the expected total of the effects of the individual herbicides employed. The synergistic effects allow the application rate to be reduced, a broader spectrum of broad-leaved weeds and grass weeds to be controlled, the herbicidal effect to take place more rapidly, the duration of action to be longer, the harmful plants to be controlled better while using only one, or few, applications, and the application period which is possible to be extended. In some cases, use of the compositions also reduces the amount of harmful constituents in the crop plant, such as nitrogen or oleic acid. The abovementioned properties and advantages are necessary under practical weed control conditions to keep agricultural crops free from undesired competing plants and thus to guarantee and/or increase the yields from the qualitative and quantitative point of view. These novel combinations markedly exceed the technical state of the art with a view to the properties described.

While the compounds according to the invention have an outstanding herbicidal activity against monocotyledonous and dicotyledonous weeds, the tolerant, or cross-tolerant, soybean plants are damaged only to a minor extent, or not at all.

Moreover, some of the compositions according to the invention have outstanding growth-regulatory properties on the soybean plants. They engage in the plants' metabolism in a regulatory manner and can thus be employed for provoking directed effects on plant constituents.

Moreover, they are also suitable for the general control and inhibition of undesired vegetative growth without simultaneously destroying the plants. An inhibition of vegetative growth is very important in a large number of monocotyledonous and dicotyledonous crops since lodging can thus be reduced, or prevented completely.

Owing to their herbicidal and plant-growth-regulatory properties, the compositions can be employed for controlling harmful plants in known tolerant or cross-tolerant soybean crops, or in tolerant or genetically engineered soybean crops.

Furthermore the herbicidal composition can have a positive effect on the vigor of the crop plant, in particular the combination have a potential to increase the nutritional uptake by the crops. They potentially also improve the crop plants's resistance to abiotic stress factors, such as draughts. These effects may lead to a reduced damage of the crop plants. With these effects the combinations of the invention benefit to an overall increase of yield of the crops.

Conventional methods of generating novel plants which have modified properties in comparison to plants occurring to date consist, for example, in traditional breeding methods and the generation of mutants. Alternatively, novel plants with altered properties can be generated with the aid of genetic engineering methods. Examples for transgenic soybean plants are given in WO2012/082548 A1 or WO2011/063411 A1.

A large number of techniques in molecular biology with the aid of which novel transgenic plants with modified properties can be generated are known in principle; see, for example, Sambrook et al., 1989, Molecular Cloning, A Laboratory Manual, 2nd Edition, Cold Spring Harbor Laboratory Press, Cold Spring Harbor, N.Y.; or Winnacker "Gene and Klone" [Genes and Clones], VCH Weinheim 2nd Edition 1996 or Christou, "Trends in Plant Science" 1 (1996) 423 431.

To carry out such genetic engineering manipulations, nucleic acid molecules which allow mutagenesis or sequence changes by recombination of DNA sequences can be introduced in plasmids. For example, the abovementioned standard methods allow base changes to be carried out, subsequences to be removed, or natural or synthetic sequences to be added. To connect the DNA fragments to each other, adaptors or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use, on the one hand, DNA molecules which encompass the entire encoding sequence of a gene product inclusive of any flanking sequences which may be present, as well as DNA molecules which only encompass portions of the encoding sequence, it being necessary for these portions to be long enough to have an antisense effect on the cells. The use of DNA sequences which have a high degree of homology to the encoding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the encoding region with DNA sequences which ensure localization in a particular compartment. Such sequences are known to those skilled in the art (see, for example, Braun et al., EMBO J. 11 (1992), 3219 3227; Wolter et al., Proc. Natl. Acad. Sci. USA 85 (1988), 846 850; Sonnewald et al., Plant J. 1 (1991), 95 106).

The transgenic plant cells can be regenerated by known techniques to give rise to whole plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

The invention therefore also relates to a method of controlling undesired vegetation in tolerant soybean crops, which comprises applying one or more herbicides of the type (A) and one or more herbicides of the type (B) to the harmful plants, parts of these plants, or the area under cultivation.

The invention also relates to the novel combinations of compounds (A)+(B) and to herbicidal compositions comprising them.

The active substance combinations according to the invention can exist not only as formulation mixes of the two components, if appropriate together with other active substances, additives and/or conventional formulation auxiliaries, which are then applied in the customary manner after dilution with water, but also as so-called tank mixes by jointly diluting the separately formulated, or partially separately formulated, components with water.

Compounds (A) and (B) or their combinations can be formulated in different ways, depending on the biological and/or chemico-physical parameters which prevail. The following are examples of general possibilities for formulations: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed-dressing materials, granules for soil application or for broadcasting, or water dispersible granules (WG), ULV formulations, microcapsules or waxes. The individual formulation types are known in principle and are described, for example, in: Winnacker-Kuchler "Chemische Technologie" [Chemical engineering], Volume 7, C. Hauser Verlag Munich, 4th Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflachenaktive Athylenoxidaddukte" [Surface-active ethylene oxide adducts], Wiss. Verlagsgesellschaft, Stuttgart 1976, Winnacker-Kuchler, "Chemische Technologie", Volume 7, C. Hauser Verlag Munich, 4th Edition 1986.

Based on these formulations, combinations with other pesticidally active substances, such as other herbicides, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active substance, also comprise ionic or non-ionic surfactants (wetters, dispersants), for example polyoxethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltauride, in addition to a diluent or inert material.

Emulsifiable concentrates are prepared by dissolving the active substance in an organic solvent, for example butanol, cyclohexanone, dimethylformamide, xylene or else higher-boiling aromatic or hydrocarbons with addition of one or more ionic or non-ionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active substance with finely divided solid materials, for example talc, natural clays such as kaolin, bentonite and pyrophyllite, or diatomateous earth. Granules can be prepared either by spraying the active substance onto adsorptive, granulated inert material or by applying active substance concentrates to the surface of carriers such as sand, kaolites or granulated inert material with the aid of binders, for example polyvinyl alcohol, sodium polyacrylate or else mineral oils. Suitable active substances may also be granulated in the manner conventionally used for the production of fertilizer granules, if desired in a mixture with fertilizers. As a rule, water-dispersible granules are prepared by processes such as spray drying, fluidized-bed granulation, disk granulation, mixing with high-speed mixers and extrusion without solid inert material.

As a rule, the agrochemical preparations comprise 0.1 to 99 percent by weight, in particular 2 to 95% by weight, of active substances of the types A and/or B, the following concentrations being customary, depending on the type of formulation: The active substance concentration in wettable powders is, for example, approximately 10 to 95% by weight, the remainder to 100% by weight being composed of customary formulation constituents. In the case of emulsifiable concentrates, the active substance concentration may amount to, for example, 5 to 80% by weight.

Formulations in the form of dusts comprise, in most cases, 5 to 20% by weight of active substance, sprayable solutions approximately 0.2 to 25% by weight of active substance.

In the case of granules such as dispersible granules, the active substance content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active substance formulations may comprise, if appropriate, the conventional adhesives, wetters, dispersants, emulsifiers, preservatives, antifreeze agents, solvents, fillers, colors, carriers, antifoams, evaporation inhibitors, pH regulators or viscosity regulators.

For example, it is known that the effect of glufosinate-ammonium (G1.2) and of its L-enantiomer can be improved by surfactants, preferably by wetters from the series of the alkyl polyglycol ether sulfates which contain, for example, 10 to 18 carbon atoms and which are used in the form of their alkali metal salts or ammonium salts, but also as the magnesium salt, such as sodium $C_{12}/C_{14}$-fatty alcohol diglycol ether sulfate (®Genapol LRO, Hoechst); see EP-A-0476555, EP-A-0048436, EP-A-0336151 or U.S. Pat. No. 4,400,196 and Proc. EWRS Symp. "Factors Affecting Herbicidal Activity and Selectivity", 227 232 (1988). Moreover, it is known that alkyl polyglycol ether sulfates are also suitable as penetrants and synergists for a series of other herbicides, inter alia also herbicides from the series of the imidazolinones; see EP-A-0502014.

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further prior to use with other inert substances.

The active substances can be applied to the plants, parts of the plants, seeds of the plants or the area under cultivation (soil of a field), preferably to the green plants and parts of the plants and, if appropriate, additionally to the soil of the field.

One possible use is the joint application of the active substances in the form of tank mixes, the concentrated formulations of the individual active substances, in optimal formulations, jointly being mixed with water in the tank and the resulting spray mixture being applied.

A joint herbicidal formulation of the combination according to the invention of the active substances (A) and (B) has the advantage of being easier to apply since the quantities of the components are already presented in the correct ratio to each other. Moreover, the adjuvants in the formulation can be matched optimally to each other, while a tank mix of different formulations may lead to undesired combinations of adjuvants.

General Formulation Examples a) A dust is obtained by mixing 10 parts by weight of an active substance/active substance mixture and 90 parts by weight of talc as inert material and comminuting the mixture in a hammer mill.
b) A wettable powder which is readily dispersible in water is obtained by mixing 25 parts by weight of an active substance/active substance mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.
c) A dispersion concentrate which is readily dispersible in water is obtained by mixing 20 parts by weight of an active substance/active substance mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to 277 C), and grinding the mixture in a ball mill to a fineness of below 5 microns.
d) An emulsifiable concentrate is obtained from 15 parts by weight of an active substance/active substance mixture, 75 parts by weight of cyclohexanone as solvent and 10 parts by weight of oxethylated nonylphenol as emulsifier.
e) Water-dispersible granules are obtained by mixing 75 parts by weight of an active substance/active substance mixture, 10 parts by weight of calcium lignosulfonate, 5 parts by weight of sodium lauryl sulfate, 3 parts by weight of polyvinyl alcohol and 7 parts by weight of kaolin, grinding the mixture on a pinned-disk mill and granulating the powder in a fluidized bed by spraying on water as granulation liquid.
f) Water-dispersible granules are also obtained by homogenizing and precomminuting, on a colloid mill, 25 parts by weight of an active substance/active substance mixture, 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-substance model.

Synergistic Effects

The synergistic effects between the active substances (A) and (B) can be tested for example as follows:

Seeds or rhizome pieces of monocotyledonous and dicotyledonous weed plants can be placed in sandy loam soil in plastic pots and covered with soil. The compositions which are formulated in the form of concentrated aqueous solutions, wettable powders or emulsion concentrates can then be applied to the surface of the soil cover in the form of an aqueous solution, suspension or emulsion at an application rate of 600 to 800 l of water/ha (converted), in various dosages. After the treatment, the pots can be placed in a greenhouse and can be kept under good growth conditions for the weeds. After the test plants will emerge, the damage to the plants or the negative effect on the emergence can be scored visually after a test period of 3 to 4 weeks by comparison with untreated controls.

Frequently, effects of the combinations according to the invention will be observed which exceed the formal total of the effects when applying the herbicides individually (=synergistic effect).

If the data of the effects observed already exceed the formal total (=E.sup.A) of the data of the experiments with individual applications, then they also exceed Colby's expected value (=E.sup.C), which is calculated by the formula which follows and which is also considered to be suggestive of synergism (cf. S. R. Colby; in Weeds 15 (1967) pp. 20 to 22): E=A+B−(AB/100) A, B denote the effect of the active substances A, or in %, for a or b g of a.s./ha; E denotes the expected value in % for a+b g a.s./ha.

At suitable low dosages, the observed data of the experiments show an effect of the combinations above Colby's expected values.

Methodology of Post-Emergence Treatments

Seeds of grass and broadleaf weeds were sown in pots (diameter: 8 cm) filled with a sandy loam soil. For the herbicide post-emergent treatment, the weeds were grown under optimal conditions up to a growth stage of BBCH 11 (1-2 leaf stage) to 14 (3-4 leaf stage) depending on species. The following weeds were used:

| Grass weeds | | Broadleaf weeds | |
|---|---|---|---|
| BRAPP | Brachiaria platyphylla | BIDPI | Bidens pilosa |
| SETFA | Setaria faberi | EPHHL | Euphorbia heterophylla |
| SETVI | Setaria viridis | PHBPU | Pharbitis purpurea |
| SORHA | Sorghum halepense | POLCO | Polygonum convolvulus |

The soybeans were grown under the same conditions as described above. The following three varieties were used in the tests:
1) W336—Transgenic soybean plants comprising a chimeric gene encoding a W336 mutant HPPD protein of Pseudomonas fluorescens (U.S. Pat. No. 6,245,968) fused to the optimized transit peptide for chloroplast targeting (U.S. Pat. No. 5,510,471), and under the control of the 35S CaMV promoter (Odell et al., 1985, Nature 313: 810-812) fused to the 5' enhancer sequence of TEV (Carrington and Freed, 1990, J. Virol. 64: 1590-1597), with as 3' transcript termination and polyadenylation region that of the CaMV 35S gene (Sanfacon et al., 1991, Genes & Development 5:141-149), abbreviated as "W336 soybean plants" herein.
2) MERLIN—conventional
3) PROTINA—conventional Two sets of soybeans reaching different growth stages at application time were prepared: one up to growth stage BBCH 11 (1-2 leaf stage) and the other up to BBCH 13 (3-4 leaf stage). Both soybean sets were treated at the same time (together with the weeds) but they were evaluated separately.

The applications were performed by post emergence treatments on the planted pots using a spray volume of 300 L water per hectare. The herbicides were applied alone and in combination as in the tables below.

The trial was conducted in the greenhouse ensuring optimal growing conditions.

The herbicidal effects were assessed 14 and 24 days following application by visual ratings comparing treated and untreated plants (0%=no effect to 100%=complete die-off).

The visual ratings are used to calculate interactions between treatments alone and combination treatments according to S. R. Colby, Weeds 15, pages 20 to 22 (1967).

The results are shown in the result tables 9 to 13 below.

TABLE 9

Metribuzin (B1); Bicyclopyrone (A6)

| No. | Growth stage | Assessment (d) | Plant species | Comp. (B) | Dose (g a.i./ha) | Effect (%) | Comp. (A) | Dose (g a.i./ha) | Effect (%) | Doses B + A (g a.i./ha) | Effect (%) | Colby calc. (%) | Difference Δ (%) |
|---|---|---|---|---|---|---|---|---|---|---|---|---|---|
| 1 | 1-2 leaf | 14 | GLXMA GM_W336 | (B1) | 80 | 25 | (A6) | 5 | 5 | 80 + 5 | 20 | 29 | −9 |
| 2 | 1-2 leaf | 14 | GLXMA Protina | (B1) | 80 | 40 | (A6) | 5 | 50 | 80 + 5 | 80 | 70 | +10 |
| 3 | 1-2 leaf | 14 | SETFA | (B1) | 80 | 30 | (A6) | 5 | 15 | 80 + 5 | 80 | 41 | +40 |
| 4 | 1-2 leaf | 14 | SORHA | (B1) | 80 | 20 | (A6) | 5 | 0 | 80 + 5 | 75 | 20 | +55 |
| 5 | 3-4 leaf | 14 | GLXMA GM_W336 | (B1) | 20 | 35 | (A6) | 20 | 30 | 20 + 20 | 30 | 55 | −25 |
| 6 | 3-4 leaf | 14 | GLXMA Protina | (B1) | 20 | 25 | (A6) | 20 | 60 | 20 + 20 | 85 | 70 | +15 |
| 7 | 3-4 leaf | 14 | BRAPP | (B1) | 20 | 15 | (A6) | 20 | 25 | 20 + 20 | 65 | 36 | +29 |
| 8 | 3-4 leaf | 14 | POLCO | (B1) | 20 | 10 | (A6) | 20 | 50 | 20 + 20 | 75 | 55 | +20 |
| 9 | 3-4 leaf | 14 | GLXMA GM_W336 | (B1) | 20 | 35 | (A6) | 10 | 25 | 20 + 10 | 35 | 51 | −16 |
| 10 | 3-4 leaf | 14 | GLXMA Protina | (B1) | 20 | 25 | (A6) | 10 | 45 | 20 + 10 | 70 | 59 | +11 |
| 11 | 3-4 leaf | 14 | BRAPP | (B1) | 20 | 15 | (A6) | 10 | 15 | 20 + 10 | 70 | 28 | +42 |
| 12 | 3-4 leaf | 14 | POLCO | (B1) | 20 | 10 | (A6) | 10 | 50 | 20 + 10 | 85 | 55 | +30 |
| 13 | 3-4 leaf | 24 | GLXMA GM_W336 | (B1) | 20 | 30 | (A6) | 20 | 30 | 20 + 20 | 30 | 51 | −21 |
| 14 | 3-4 leaf | 24 | GLXMA Merlin | (B1) | 20 | 40 | (A6) | 20 | 50 | 20 + 20 | 85 | 70 | +15 |
| 15 | 3-4 leaf | 24 | BRAPP | (B1) | 20 | 10 | (A6) | 20 | 15 | 20 + 20 | 60 | 24 | +37 |
| 16 | 3-4 leaf | 24 | BIDPI | (B1) | 20 | 5 | (A6) | 20 | 30 | 20 + 20 | 65 | 34 | +32 |
| 17 | 3-4 leaf | 24 | GLXMA GM_W336 | (B1) | 20 | 30 | (A6) | 10 | 25 | 20 + 10 | 35 | 48 | −13 |
| 18 | 3-4 leaf | 24 | GLXMA Merlin | (B1) | 20 | 40 | (A6) | 10 | 50 | 20 + 10 | 85 | 70 | +15 |
| 19 | 3-4 leaf | 24 | EPHHL | (B1) | 20 | 20 | (A6) | 10 | 40 | 20 + 10 | 70 | 52 | +18 |
| 20 | 3-4 leaf | 24 | POLCO | (B1) | 20 | 10 | (A6) | 10 | 35 | 20 + 10 | 80 | 42 | +39 |

TABLE 10

Metribuzin (B1); Isoxaflutole (A4)

| No. | Growth stage | Assessment (d) | Plant species | Comp. (B) | Dose (g a.i./ha) | Effect (%) | Comp. (A) | Dose (g a.i./ha) | Effect (%) | Doses B + A (g a.i./ha) | Effect (%) | Colby calc. (%) | Difference Δ (%) |
|---|---|---|---|---|---|---|---|---|---|---|---|---|---|
| 21 | 3-4 leaf | 14 | GLXMA GM_W336 | (B1) | 40 | 35 | (A4) | 10 | 10 | 40 + 10 | 35 | 42 | −7 |
| 22 | 3-4 leaf | 14 | GLXMA Protina | (B1) | 40 | 35 | (A4) | 10 | 35 | 40 + 10 | 70 | 58 | +12 |
| 23 | 3-4 leaf | 14 | BRAPP | (B1) | 40 | 45 | (A4) | 10 | 15 | 40 + 10 | 70 | 53 | +17 |
| 24 | 3-4 leaf | 14 | PHBPU | (B1) | 40 | 10 | (A4) | 10 | 40 | 40 + 10 | 75 | 46 | +29 |
| 25 | 1-2 leaf | 24 | GLXMA GM_W336 | (B1) | 80 | 30 | (A4) | 20 | 10 | 80 + 20 | 25 | 37 | −12 |
| 26 | 1-2 leaf | 24 | GLXMA Protina | (B1) | 80 | 40 | (A4) | 20 | 75 | 80 + 20 | 97 | 85 | +12 |
| 27 | 1-2 leaf | 24 | SETVI | (B1) | 80 | 10 | (A4) | 20 | 10 | 80 + 20 | 98 | 19 | +79 |
| 28 | 1-2 leaf | 24 | SORHA | (B1) | 80 | 10 | (A4) | 20 | 40 | 80 + 20 | 93 | 46 | +47 |

TABLE 11

| No. | Growth stage | Assessment (d) | Plant species | Comp. (B) | Dose (g a.i./ha) | Effect (%) | Comp. (A) | Dose (g a.i./ha) | Effect (%) | Doses B + A (g a.i./ha) | Effect (%) | Colby calc. (%) | Difference Δ (%) |
|---|---|---|---|---|---|---|---|---|---|---|---|---|---|
| | | | | Metribuzin (B1); Mesotrione (A2) | | | | | | | | | |
| 29 | 1-2 leaf | 14 | GLXMA GM_W336 | (B1) | 20 | 20 | (A2) | 20 | 20 | 20 + 20 | 25 | 36 | −11 |
| 30 | 1-2 leaf | 14 | GLXMA Protina | (B1) | 20 | 20 | (A2) | 20 | 45 | 20 + 20 | 95 | 56 | +39 |
| 31 | 1-2 leaf | 14 | BRAPP | (B1) | 20 | 15 | (A2) | 20 | 50 | 20 + 20 | 95 | 58 | +38 |
| 32 | 1-2 leaf | 14 | EPHHL | (B1) | 20 | 45 | (A2) | 20 | 30 | 20 + 20 | 80 | 62 | +19 |
| 33 | 3-4 leaf | 14 | GLXMA GM_W336 | (B1) | 80 | 35 | (A2) | 5 | 15 | 80 + 5 | 30 | 45 | −15 |
| 34 | 3-4 leaf | 14 | GLXMA Merlin | (B1) | 80 | 50 | (A2) | 5 | 30 | 80 + 5 | 75 | 65 | +10 |
| 35 | 3-4 leaf | 14 | SORHA | (B1) | 80 | 20 | (A2) | 5 | 0 | 80 + 5 | 70 | 20 | +50 |
| 36 | 3-4 leaf | 14 | POLCO | (B1) | 80 | 40 | (A2) | 5 | 20 | 80 + 5 | 90 | 52 | +38 |
| 37 | 3-4 leaf | 14 | GLXMA GM_W336 | (B1) | 20 | 35 | (A2) | 20 | 25 | 20 + 20 | 25 | 51 | −26 |
| 38 | 3-4 leaf | 14 | GLXMA Protina | (B1) | 20 | 25 | (A2) | 20 | 50 | 20 + 20 | 80 | 63 | +18 |
| 39 | 3-4 leaf | 14 | SORHA | (B1) | 20 | 20 | (A2) | 20 | 15 | 20 + 20 | 50 | 32 | +18 |
| 40 | 3-4 leaf | 14 | POLCO | (B1) | 20 | 10 | (A2) | 20 | 65 | 20 + 20 | 93 | 69 | +25 |
| 41 | 1-2 leaf | 24 | GLXMA GM_W336 | (B1) | 80 | 30 | (A2) | 10 | 15 | 80 + 10 | 20 | 41 | −21 |
| 42 | 1-2 leaf | 24 | GLXMA Protina | (B1) | 80 | 40 | (A2) | 10 | 20 | 80 + 10 | 75 | 52 | +23 |
| 43 | 1-2 leaf | 24 | EPHHL | (B1) | 80 | 65 | (A2) | 10 | 10 | 80 + 10 | 100 | 69 | +32 |
| 44 | 1-2 leaf | 24 | POLCO | (B1) | 80 | 20 | (A2) | 10 | 20 | 80 + 10 | 100 | 36 | +64 |
| 45 | 1-2 leaf | 24 | GLXMA GM_W336 | (B1) | 80 | 30 | (A2) | 5 | 15 | 80 + 5 | 15 | 41 | −26 |
| 46 | 1-2 leaf | 24 | GLXMA Protina | (B1) | 80 | 40 | (A2) | 5 | 15 | 80 + 5 | 80 | 49 | +31 |
| 47 | 1-2 leaf | 24 | SETVI | (B1) | 80 | 10 | (A2) | 5 | 0 | 80 + 5 | 100 | 10 | +90 |
| 48 | 1-2 leaf | 24 | SORHA | (B1) | 80 | 10 | (A2) | 5 | 0 | 80 + 5 | 50 | 10 | +40 |
| 49 | 1-2 leaf | 24 | GLXMA GM_W336 | (B1) | 40 | 10 | (A2) | 20 | 25 | 40 + 20 | 15 | 33 | −18 |
| 50 | 1-2 leaf | 24 | GLXMA Protina | (B1) | 40 | 15 | (A2) | 20 | 40 | 40 + 20 | 80 | 49 | +31 |
| 51 | 1-2 leaf | 24 | BRAPP | (B1) | 40 | 10 | (A2) | 20 | 35 | 40 + 20 | 85 | 42 | +44 |
| 52 | 1-2 leaf | 24 | BIDPI | (B1) | 40 | 45 | (A2) | 20 | 20 | 40 + 20 | 93 | 56 | +37 |
| 53 | 1-2 leaf | 24 | GLXMA GM_W336 | (B1) | 20 | 10 | (A2) | 20 | 25 | 20 + 20 | 20 | 33 | −13 |
| 54 | 1-2 leaf | 24 | GLXMA Protina | (B1) | 20 | 15 | (A2) | 20 | 40 | 20 + 20 | 93 | 49 | +44 |
| 55 | 1-2 leaf | 24 | BIDPI | (B1) | 20 | 5 | (A2) | 20 | 20 | 20 + 20 | 93 | 24 | +69 |
| 56 | 1-2 leaf | 24 | EPHHL | (B1) | 20 | 20 | (A2) | 20 | 10 | 20 + 20 | 75 | 28 | +47 |
| 57 | 1-2 leaf | 24 | GLXMA GM_W336 | (B1) | 20 | 10 | (A2) | 10 | 15 | 20 + 10 | 10 | 24 | −14 |
| 58 | 1-2 leaf | 24 | GLXMA Protina | (B1) | 20 | 15 | (A2) | 10 | 20 | 20 + 10 | 93 | 32 | +61 |
| 59 | 1-2 leaf | 24 | BRAPP | (B1) | 20 | 10 | (A2) | 10 | 25 | 20 + 10 | 80 | 33 | +48 |
| 60 | 1-2 leaf | 24 | PHBPU | (B1) | 20 | 0 | (A2) | 10 | 75 | 20 + 10 | 95 | 75 | +20 |

TABLE 12

| No. | Growth stage | Assessment (d) | Plant species | Comp. (B) | Dose (g a.i./ha) | Effect (%) | Comp. (A) | Dose (g a.i./ha) | Effect (%) | Doses B + A (g a.i./ha) | Effect (%) | Colby calc. (%) | Difference Δ (%) |
|---|---|---|---|---|---|---|---|---|---|---|---|---|---|
| | | | | Metribuzin (B1); Tembotrione (A1) | | | | | | | | | |
| 61 | 3-4 leaf | 14 | GLXMA GM_W336 | (B1) | 40 | 35 | (A1) | 5 | 20 | 40 + 5 | 40 | 48 | −8 |
| 62 | 3-4 leaf | 14 | GLXMA Protina | (B1) | 40 | 35 | (A1) | 5 | 55 | 40 + 5 | 95 | 71 | +24 |
| 63 | 3-4 leaf | 14 | BRAPP | (B1) | 40 | 45 | (A1) | 5 | 25 | 40 + 5 | 90 | 59 | +31 |
| 64 | 3-4 leaf | 14 | POLCO | (B1) | 40 | 40 | (A1) | 5 | 10 | 40 + 5 | 85 | 46 | +39 |
| 65 | 3-4 leaf | 14 | GLXMA GM_W336 | (B1) | 20 | 35 | (A1) | 5 | 20 | 20 + 5 | 40 | 48 | −8 |
| 66 | 3-4 leaf | 14 | GLXMA Protina | (B1) | 20 | 25 | (A1) | 5 | 55 | 20 + 5 | 85 | 66 | +19 |

TABLE 12-continued

Metribuzin (B1); Tembotrione (A1)

| No. | Growth stage | Assessment (d) | Plant species | Comp. (B) | Dose (g a.i./ha) | Effect (%) | Comp. (A) | Dose (g a.i./ha) | Effect (%) | Doses B + A (g a.i./ha) | Effect (%) | Colby calc. (%) | Difference Δ (%) |
|---|---|---|---|---|---|---|---|---|---|---|---|---|---|
| 67 | 3-4 leaf | 14 | BRAPP | (B1) | 20 | 15 | (A1) | 5 | 25 | 20 + 5 | 75 | 36 | +39 |
| 68 | 3-4 leaf | 14 | BIDPI | (B1) | 20 | 40 | (A1) | 5 | 10 | 20 + 5 | 75 | 46 | +29 |
| 69 | 1-2 leaf | 24 | GLXMA GM_W336 | (B1) | 80 | 30 | (A1) | 10 | 15 | 80 + 10 | 20 | 41 | −21 |
| 70 | 1-2 leaf | 24 | GLXMA Merlin | (B1) | 80 | 10 | (A1) | 10 | 80 | 80 + 10 | 93 | 82 | +11 |
| 71 | 1-2 leaf | 24 | BRAPP | (B1) | 80 | 35 | (A1) | 10 | 10 | 80 + 10 | 85 | 42 | +44 |
| 72 | 1-2 leaf | 24 | SETVI | (B1) | 80 | 10 | (A1) | 10 | 40 | 80 + 10 | 100 | 46 | +54 |
| 73 | 1-2 leaf | 24 | GLXMA GM_W336 | (B1) | 80 | 30 | (A1) | 5 | 15 | 80 + 5 | 20 | 41 | −21 |
| 74 | 1-2 leaf | 24 | GLXMA Merlin | (B1) | 80 | 10 | (A1) | 5 | 75 | 80 + 5 | 90 | 78 | +13 |
| 75 | 1-2 leaf | 24 | BRAPP | (B1) | 80 | 35 | (A1) | 5 | 10 | 80 + 5 | 70 | 42 | +29 |
| 76 | 1-2 leaf | 24 | SETVI | (B1) | 80 | 10 | (A1) | 5 | 40 | 80 + 5 | 98 | 46 | +52 |
| 77 | 1-2 leaf | 24 | GLXMA GM_W336 | (B1) | 40 | 10 | (A1) | 10 | 15 | 40 + 10 | 10 | 24 | −14 |
| 78 | 1-2 leaf | 24 | GLXMA Merlin | (B1) | 40 | 0 | (A1) | 10 | 80 | 40 + 10 | 93 | 80 | +13 |
| 79 | 1-2 leaf | 24 | BRAPP | (B1) | 40 | 10 | (A1) | 10 | 10 | 40 + 10 | 80 | 19 | +61 |
| 80 | 1-2 leaf | 24 | SETVI | (B1) | 40 | 50 | (A1) | 10 | 40 | 40 + 10 | 98 | 70 | +28 |
| 81 | 1-2 leaf | 24 | GLXMA GM_W336 | (B1) | 40 | 10 | (A1) | 5 | 15 | 40 + 5 | 10 | 24 | −14 |
| 82 | 1-2 leaf | 24 | GLXMA Protina | (B1) | 40 | 15 | (A1) | 5 | 75 | 40 + 5 | 95 | 79 | +16 |
| 83 | 1-2 leaf | 24 | SORHA | (B1) | 40 | 10 | (A1) | 5 | 20 | 40 + 5 | 65 | 28 | +37 |
| 84 | 1-2 leaf | 24 | POLCO | (B1) | 40 | 15 | (A1) | 5 | 0 | 40 + 5 | 80 | 15 | +65 |
| 85 | 1-2 leaf | 24 | GLXMA GM_W336 | (B1) | 40 | 10 | (A1) | 2.5 | 15 | 40 + 2.5 | 5 | 24 | −19 |
| 86 | 1-2 leaf | 24 | GLXMA Protina | (B1) | 40 | 15 | (A1) | 2.5 | 65 | 40 + 2.5 | 95 | 70 | +25 |
| 87 | 1-2 leaf | 24 | SETFA | (B1) | 40 | 10 | (A1) | 2.5 | 0 | 40 + 2.5 | 50 | 10 | +40 |
| 88 | 1-2 leaf | 24 | POLCO | (B1) | 40 | 15 | (A1) | 2.5 | 0 | 40 + 2.5 | 65 | 15 | +50 |

TABLE 13

Metribuzin (B1); Topramezone (A5)

| No. | Growth stage | Assessment (d) | Plant species | Comp. (B) | Dose (g a.i./ha) | Effect (%) | Comp. (A) | Dose (g a.i./ha) | Effect (%) | Doses B + A (g a.i./ha) | Effect (%) | Colby calc. (%) | Difference Δ (%) |
|---|---|---|---|---|---|---|---|---|---|---|---|---|---|
| 89 | 3-4 leaf | 14 | GLXMA GM_W336 | (B1) | 20 | 35 | (A5) | 3 | 30 | 20 + 3 | 40 | 55 | −15 |
| 90 | 3-4 leaf | 14 | GLXMA Protina | (B1) | 20 | 25 | (A5) | 3 | 50 | 20 + 3 | 80 | 63 | +18 |
| 91 | 3-4 leaf | 14 | SORHA | (B1) | 20 | 20 | (A5) | 3 | 15 | 20 + 3 | 50 | 32 | +18 |
| 92 | 3-4 leaf | 14 | BIDPI | (B1) | 20 | 40 | (A5) | 3 | 25 | 20 + 3 | 80 | 55 | +25 |
| 93 | 1-2 leaf | 24 | GLXMA GM_W336 | (B1) | 40 | 10 | (A5) | 1.5 | 15 | 40 + 1.5 | 15 | 24 | −9 |
| 94 | 1-2 leaf | 24 | GLXMA Merlin | (B1) | 40 | 0 | (A5) | 1.5 | 55 | 40 + 1.5 | 65 | 55 | +10 |
| 95 | 1-2 leaf | 24 | SETFA | (B1) | 40 | 10 | (A5) | 1.5 | 30 | 40 + 1.5 | 95 | 37 | +58 |
| 96 | 1-2 leaf | 24 | PHBPU | (B1) | 40 | 0 | (A5) | 1.5 | 30 | 40 + 1.5 | 65 | 30 | +35 |
| 97 | 3-4 leaf | 24 | GLXMA GM_W336 | (B1) | 20 | 30 | (A5) | 3 | 30 | 20 + 3 | 40 | 51 | −11 |
| 98 | 3-4 leaf | 24 | GLXMA Protina | (B1) | 20 | 35 | (A5) | 3 | 50 | 20 + 3 | 80 | 68 | +13 |
| 99 | 3-4 leaf | 24 | SORHA | (B1) | 20 | 0 | (A5) | 3 | 10 | 20 + 3 | 45 | 10 | +35 |
| 100 | 3-4 leaf | 24 | BIDPI | (B1) | 20 | 5 | (A5) | 3 | 10 | 20 + 3 | 60 | 15 | +46 |

The invention claimed is:

1. A method for controlling harmful plants in soybean crop comprising applying as the sole herbically active components,
(A) an effective amount of active substance with HPPD inhibiting activity
(A7) N,O-chelator, according to formula (I)

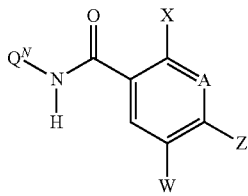

wherein
X is Cl;
A is C—Y, wherein
Y is SMe;
Z is CF$_3$;
W is hydrogen;
Q$^N$ is

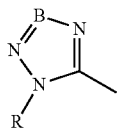

wherein
B is nitrogen;
R is Me,
and
(B) an effective amount of the active substance metribuzine (B1)
wherein the weight ratio of (A) to (B) is 1:1 to 1:10, wherein (A) and (B) are used in amounts to provide synergistic results
to soybean crops that are from a soybean culture that is tolerant against said (A) and (B), and wherein (A) and (B) are applied together.

2. A method according to claim 1, wherein the soybean culture comprises a heterologous gene that confers HPPD inhibitor tolerance.

3. A method according to claim 2, wherein the HPPD tolerance of the soybean cultures is conferred by the hppdPF W336 gene.

4. A method according to claim 2, wherein the HPPD tolerance of the soybean cultures is conferred by the avhppd-03 gene.

5. A method according to claim 1, wherein the soybean culture or parts or seeds thereof comprise the SYHT0H2 event.

6. A method according to claim 1, wherein the soybean culture or parts or seeds thereof comprise the EE-GM3 event.

7. Method for controlling one or more harmful plants in one or more soybean cultures comprising jointly applying, pre-emergence, post-emergence or pre- and post-emergence to the plants, parts of the plants, seeds of the plants or the area under cultivation as sole herbicidally active components an effective amount of (B) metribuzine and an effective amount of (A) active substance with HPPD inhibiting activity
(A7) N,O-chelator, according to formula (I)

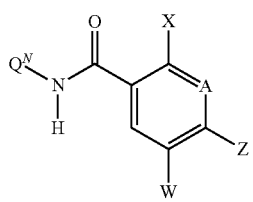

wherein
X is Cl;
A is C—Y, wherein
Y is SMe;
Z is CF$_3$;
W is hydrogen;
Q$^N$ is

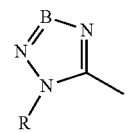

wherein
B is nitrogen;
R is Me
wherein the weight ratio of (A) to (B) is 1:1 to 1:10, and wherein (A) and (B) are used in amounts to provide synergistic results.

8. Method according to claim 7 wherein the soybean cultures are tolerant against the active substances (A) and (B) applied thereto.

9. A composition for controlling harmful plants in soybean crop comprising as the sole herbically active components
(A) an effective amount of active substance with HPPD inhibiting activity
(A7) N,O-chelator, according to formula (I)

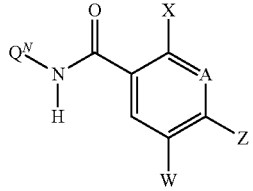

wherein
X is Cl;
A is C—Y, wherein
Y is SMe;
Z is CF$_3$;
W is hydrogen;

$Q^N$ is
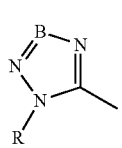
$Q^{N-1}$
wherein
B is nitrogen;
R is Me,
   and
   (B) an effective amount of the active substance metribuzine (B1)
wherein the weight ratio of (A) to (B) is 1:1 to 1:10 and wherein (A) and (B) are present in amounts to provide synergistic results.
* * * * *